(12) United States Patent
Hatanaka et al.

(10) Patent No.: US 9,827,268 B2
(45) Date of Patent: Nov. 28, 2017

(54) CURABLE CALCIUM PHOSPHATE COMPOSITION FOR BIOLOGICAL HARD TISSUE REPAIR, BONE REPAIR MATERIAL, AND VARIOUS DENTAL MATERIALS

(71) Applicant: KURARAY NORITAKE DENTAL INC., Kurashiki-shi (JP)

(72) Inventors: Kenji Hatanaka, Niigata (JP); Shumei Ishihara, Niigata (JP)

(73) Assignee: KURARAY NORITAKE DENTAL INC., Kurashiki-shi (JP)

( * ) Notice: Subject to any disclaimer, the term of this patent is extended or adjusted under 35 U.S.C. 154(b) by 46 days.

(21) Appl. No.: 14/910,140

(22) PCT Filed: Aug. 4, 2014

(86) PCT No.: PCT/JP2014/004076
§ 371 (c)(1),
(2) Date: Feb. 4, 2016

(87) PCT Pub. No.: WO2015/019600
PCT Pub. Date: Feb. 12, 2015

(65) Prior Publication Data
US 2016/0175355 A1    Jun. 23, 2016

(30) Foreign Application Priority Data

Aug. 6, 2013   (JP) ................................. 2013-163389

(51) Int. Cl.
| | | |
|---|---|---|
| A61K 33/10 | (2006.01) | |
| A61K 33/42 | (2006.01) | |
| A61K 6/00 | (2006.01) | |
| A61K 6/033 | (2006.01) | |
| A61L 27/12 | (2006.01) | |
| A61K 6/06 | (2006.01) | |
| A61M 25/00 | (2006.01) | |

(52) U.S. Cl.
CPC ................ *A61K 33/42* (2013.01); *A61K 6/00* (2013.01); *A61K 6/0017* (2013.01); *A61K 6/0038* (2013.01); *A61K 6/0085* (2013.01); *A61K 6/033* (2013.01); *A61K 6/0643* (2013.01); *A61K 33/10* (2013.01); *A61L 27/12* (2013.01); *A61L 2430/02* (2013.01); *A61L 2430/12* (2013.01); *A61M 2025/0019* (2013.01)

(58) Field of Classification Search
CPC .......... A61K 33/10; A61K 33/42; A61K 6/00; A61K 6/0038; A61K 6/0085; A61K 6/033; A61K 6/0643
See application file for complete search history.

(56) References Cited

U.S. PATENT DOCUMENTS

| | | | |
|---|---|---|---|
| 5,993,535 A | 11/1999 | Sawamura et al. | |
| 2007/0041906 A1* | 2/2007 | Lidgren ............... | A61K 9/0024 424/9.4 |
| 2008/0152687 A1* | 6/2008 | Thorne .................. | A61K 33/42 424/423 |
| 2009/0048145 A1* | 2/2009 | Hellerbrand .......... | A61L 27/446 514/1.1 |
| 2010/0236449 A1* | 9/2010 | Hashimoto ............ | A61K 6/033 106/35 |
| 2012/0027829 A1 | 2/2012 | Hashimoto et al. | |
| 2013/0189337 A1 | 7/2013 | Hashimoto et al. | |
| 2013/0251767 A1 | 9/2013 | Hashimoto et al. | |

FOREIGN PATENT DOCUMENTS

| | | |
|---|---|---|
| FR | 2 830 249 A1 | 4/2003 |
| JP | 10-504467 A | 5/1998 |
| JP | 11-130491 A | 5/1999 |
| JP | 2000-169200 A | 6/2000 |
| JP | 2007-190169 A | 8/2007 |
| WO | 95/08319 A1 | 3/1995 |
| WO | WO 00/78270 A1 | 12/2000 |
| WO | 2010/113800 A1 | 10/2010 |
| WO | 2010/113801 A1 | 10/2010 |
| WO | 2012/046667 A1 | 4/2012 |

OTHER PUBLICATIONS

International Search Report dated Nov. 4, 2014, in PCT/JP2014/004076 Filed Aug. 4, 2014.
Sariibrahimoglu, et al., "Effect of calcium carbonate on hardening, physicochemical properties, and in vitro degradation of injectable calcium phosphate cements," Journal of Biomedical Materials Research A, vol. 100A, Issue 3, 10 pages, 2012.
Extended European Search Report dated Jan. 11, 2017 in Patent Application No. 14834444.3.

* cited by examiner

*Primary Examiner* — Kyle Purdy
(74) *Attorney, Agent, or Firm* — Oblon, McClelland, Maier & Neustadt, L.L.P.

(57) ABSTRACT

The present invention provides a curable calcium phosphate composition for biological hard tissue repair that yields a cured product excellent in durability in a wet environment such as in a body or an oral cavity. The present invention relates to a curable calcium phosphate composition for biological hard tissue repair, including tetracalcium phosphate particles (A), calcium hydrogen phosphate particles (B), calcium carbonate particles (C), and water (D), the curable calcium phosphate composition including 5 to 75 parts by weight of the tetracalcium phosphate particles (A), 10 to 70 parts by weight of the calcium hydrogen phosphate particles (B), and 2 to 50 parts by weight of the calcium carbonate particles (C) per 100 parts by weight of the total of the tetracalcium phosphate particles (A), the calcium hydrogen phosphate particles (B), and the calcium carbonate particles (C).

14 Claims, No Drawings

CURABLE CALCIUM PHOSPHATE COMPOSITION FOR BIOLOGICAL HARD TISSUE REPAIR, BONE REPAIR MATERIAL, AND VARIOUS DENTAL MATERIALS

TECHNICAL FIELD

The present invention relates to a curable calcium phosphate composition for biological hard tissue repair. The present invention also relates to a bone repair material and various dental materials including the curable calcium phosphate composition.

BACKGROUND ART

Hydroxyapatite ($Ca_{10}(PO_4)_6(OH)_2$), obtainable by sintering of a calcium phosphate powder, is a main component of biological hard tissues such as bones and teeth and has biocompatibility. With this in mind, the use of hydroxyapatite as a repair material for a missing part or a cavity in a biological hard tissue has been reported. A material including hydroxyapatite as thus described is indeed excellent in biocompatibility but insufficient in formability, and may therefore be difficult to apply to a repair area of complicated shape.

Cement-type calcium phosphate compositions, i.e., calcium phosphate compositions having curability, are known to gradually convert to bioabsorbable hydroxyapatite in a living body or an oral cavity and be able to unite with a biological hard tissue while retaining its shape. Such curable calcium phosphate compositions not only have excellent biocompatibility but also have formability, and are therefore considered easy to apply to an area of complicated shape.

Various types of curable calcium phosphate compositions have been developed thus far. For example, Patent Literature 1 describes a rapid-curing calcium phosphate cement inducing at least one of a calcium hydrogen phosphate anhydrous powder and a calcium hydrogen phosphate dihydrate powder which have a specific surface area of 1 to 50 $m^2/g$. Even when kneading is performed with only the addition of water to a liquid material but without the addition of any acid, this cement rapidly cures, and a cured product of calcium phosphate having a high compressive strength can be obtained. However, the rapid-curing calcium phosphate cement described in Patent Literature 1 has a problem in that the strength of the cured product decreases over time in a wet environment.

Patent Literature 2 describes a calcium phosphate powdery composition composed of tetracalcium phosphate particles and calcium hydrogen phosphate particles, the calcium phosphate powdery composition containing 0.001 to 1 parts by weight of water per 100 parts by weight of the total of the tetracalcium phosphate particles and the calcium hydrogen phosphate particles. The curing time of this composition is in an appropriate range, and its workability is good. Additionally, with this composition, a cured product of calcium phosphate having high mechanical strength is obtained. However, the calcium phosphate powdery composition described in Patent Literature 2 has room for improvement in that the strength of the cured product decreases over time in a wet environment.

Patent Literature 3 describes a calcium phosphate cement which self-cures to hydroxyapatite at ambient temperatures, the calcium phosphate cement including an additional source of calcium and a calcium phosphate salt having a calcium-to-phosphorous molar ratio of less than 5/3 which is other than tetracalcium phosphate. However, the calcium phosphate cement described in Patent Literature 3 has a problem in that the strength of the cured product decreases over time in a wet environment.

Patent Literature 4 describes a dentinal tubule sealing material containing poorly-soluble calcium phosphate particles, a phosphorus-free calcium compound, and water. According to this literature, it has been confirmed that when the sealing material obtained as a paste is rubbed on dentin with a microbrush for 30 seconds, dentinal tubules can be sealed with the sealing material, and a high dentin penetration inhibition ratio can be achieved. However, the dentinal tubule sealing material described in Patent Literature 4 has room for improvement in terms of the durability of the resulting sealing product.

Patent Literature 5 proposes a method including: mixing a powder containing tetracalcium phosphate particles and an alkali metal phosphate with a liquid containing water as a main component; and applying the obtained aqueous paste to dentin surface. This method enables sealing of a large proportion of dentinal tubules, and can therefore be expected to effectively inhibit pain. However, the method described in Patent Literature 5 has room for improvement in terms of the durability of the resulting sealing product.

CITATION LIST

Patent Literature

Patent Literature 1: JP 2000-169200 A
Patent Literature 2: JP 2007-190169 A
Patent Literature 3: JP 10-504467 A
Patent Literature 4: WO 2012/046667 A1
Patent Literature 5: WO 2010/113800 A1

SUMMARY OF INVENTION

Technical Problem

The present invention aims to provide a curable calcium phosphate composition for biological hard tissue repair that yields a cured product excellent in durability in a wet environment such as in a body or an oral cavity.

Solution to Problem

The present invention is a curable calcium phosphate composition for biological hard tissue repair, including tetracalcium phosphate particles (A), calcium hydrogen phosphate particles (B), calcium carbonate particles (C), and water (D), the curable calcium phosphate composition including 5 to 75 parts by weight of the tetracalcium phosphate particles (A), 10 to 70 parts by weight of the calcium hydrogen phosphate particles (B), and 2 to 50 parts by weight of the calcium carbonate particles (C) per 100 parts by weight of the total of the tetracalcium phosphate particles (A), the calcium hydrogen phosphate particles (B), and the calcium carbonate particles (C).

The curable calcium phosphate composition of the present invention for biological hard tissue repair preferably further includes 0.5 to 15 parts by weight of an alkali metal phosphate (E) per 100 parts by weight of the total of the tetracalcium phosphate particles (A), the calcium hydrogen phosphate particles (B), and the calcium carbonate particles (C). The alkali metal phosphate (E) is preferably at least one selected from the group consisting of disodium hydrogen phosphate and sodium dihydrogen phosphate.

In the curable calcium phosphate composition of the present invention for biological hard tissue repair, it is preferable that the tetracalcium phosphate particles (A) have an average particle diameter of 0.5 to 30 μm, the calcium hydrogen phosphate particles (B) have an average particle diameter of 0.1 to 7.5 μm, and the calcium carbonate particles (C) have an average particle diameter of 0.1 to 30 μm.

One preferred embodiment of the present invention is a curable calcium phosphate composition as defined above, in which a weight ratio ((A+B+C)/D) of the total of the tetracalcium phosphate particles (A), the calcium hydrogen phosphate particles (B), and the calcium carbonate particles (C) to the water (D) is 1.8 to 5.0. The embodiment including the curable calcium phosphate composition is suitable for a bone repair material, a dental filling restorative material, a dental lining material, a dental luting material, a dental temporary sealing material, a dental sealant, a dental temporary cementation material, a dental root canal filling material, and a dental coating material.

Another preferred embodiment of the present invention is a curable calcium phosphate composition as defined above in which a weight ratio ((A+B+C)/D) of the total of the tetracalcium phosphate particles (A), the calcium hydrogen phosphate particles (B), and the calcium carbonate particles (C) to the water (D) is 0.5 to 1.8. The embodiment including the curable calcium phosphate composition is suitable for a dental dentinal tubule sealing material.

Advantageous Effects of Invention

According to the present invention, there is provided a curable calcium phosphate composition for biological hard tissue repair that yields a cured product excellent in durability in a wet environment such as in a body or an oral cavity. This allows the provision of a biological hard tissue repair material (e.g., a bone repair material, a dental material, etc.) that yields a cured product excellent in durability in a wet environment such as in a body or an oral cavity.

DESCRIPTION OF EMBODIMENTS

The present invention is a curable calcium phosphate composition for biological hard tissue repair, including tetracalcium phosphate particles (A), calcium hydrogen phosphate particles (B), calcium carbonate particles (C), and water (D), the curable calcium phosphate composition including 5 to 75 parts by weight of the tetracalcium phosphate particles (A), 10 to 70 parts by weight of the calcium hydrogen phosphate particles (B), and 2 to 50 parts by weight of the calcium carbonate particles (C) per 100 parts by weight of the total of the tetracalcium phosphate particles (A), the calcium hydrogen phosphate particles (B), and the calcium carbonate particles (C).

A calcium phosphate composition containing the tetracalcium phosphate particles (A) and the calcium hydrogen phosphate particles (B) is known to cure along with production of thermally-stable hydroxyapatite when the composition is kneaded in the presence of water. A calcium phosphate composition containing the calcium hydrogen phosphate particles (B) and a phosphorus-free calcium compound (e.g., calcium carbonate, calcium oxide, calcium hydroxide, etc.) is also known to cure along with production of thermally-stable hydroxyapatite when the composition is kneaded in the presence of water.

In developing a curable calcium phosphate composition that yields a cured product excellent in durability in a wet environment, the present inventors have found for a composition including the tetracalcium phosphate particles (A), the calcium hydrogen phosphate particles (B), the calcium carbonate particles (C), and the water (D) that a cured product of the composition uniquely shows excellent durability in a wet environment only when the tetracalcium phosphate particles (A), the calcium hydrogen phosphate particles (B), and the calcium carbonate particles (C) are contained in specified amounts relative to the total of the tetracalcium phosphate particles (A), the calcium hydrogen phosphate particles (B), and the calcium carbonate particles (C). As demonstrated by Examples and Comparative Examples given later, a cured product of a calcium phosphate composition including only a combination of the tetracalcium phosphate particles (A) with the calcium hydrogen phosphate particles (B) has low durability in a wet environment. Also, a cured product of a calcium phosphate composition including only a combination of the calcium hydrogen phosphate particles (B) with the calcium carbonate particles (C) or particles of a phosphorus-free calcium compound also has low durability in a wet environment. The use of particles of various phosphorus-free calcium compounds instead of the calcium carbonate particles (C) does not provide sufficient curability. With the contents of the tetracalcium phosphate particles (A), the calcium hydrogen phosphate particles (B), and the calcium carbonate particles (C) being outside the specified ranges, sufficient curability is not provided or the cured product has low durability in a wet environment. Thus, it is primarily important, as in the present invention, to use a combination of specified components including the tetracalcium phosphate particles (A), the calcium hydrogen phosphate particles (B), and the calcium carbonate particles (C), in a curable calcium phosphate composition. Furthermore, it is important that the content of the tetracalcium phosphate particles (A) is 5 to 75 parts by weight, the content of the calcium hydrogen phosphate particles (B) is 10 to 70 parts by weight, and the content of the calcium carbonate particles (C) is 2 to 50 parts by weight, per 100 parts by weight of the total of the tetracalcium phosphate particles (A), the calcium hydrogen phosphate particles (B), and the calcium carbonate particles (C).

In the present invention, the phrase "durability in a wet environment" refers to the property of undergoing little decrease in strength (compressive strength in particular) over time in a wet environment such as in a body or an oral cavity and exhibiting resistance to acid over a long period of time in a wet environment such as in a body or an oral cavity (which is prone to acid generation).

The tetracalcium phosphate particles (A) used in the present invention are not particularly limited. When the composition of the present invention is used in a bone repair material or in any of dental materials such as a filling restorative material, a lining material, a luting material, a temporary sealing material, a root canal filling material, a temporary cementation material, a coating material, and a sealant, the average particle diameter of the particles (A) is preferably 0.5 to 30 μm. When the average particle diameter is less than 0.5 μm, the tetracalcium phosphate particles (A) are so excessively dissolved that the resulting aqueous solution has a high pH. This may hinder smooth precipitation of hydroxyapatite, thereby reducing the durability of the cured product. The average particle diameter is preferably 3.0 μm or more and more preferably 5.0 μm or more. When the average particle diameter is more than 30 μm, a paste obtained by mixing with the water (D) may suffer deterioration in quality, such as having insufficient viscosity or having increased roughness. The average particle diameter is preferably 20.0 μm or less and more preferably 15.0 μm or less. Herein, the average particle diameter of the tetracalcium phosphate particles (A) used in the present invention is a median diameter calculated based on measurement performed using a laser diffraction particle size distribution analyzer.

When the composition of the present invention is used in a dentinal tubule sealing material or the like, the average particle diameter of the tetracalcium phosphate particles (A) used in the present invention is preferably 0.5 to 10 μm. When the average particle diameter is less than 0.5 μm, the tetracalcium phosphate particles (A) are so excessively dissolved that the resulting aqueous solution has a high pH. This may hinder smooth precipitation of hydroxyapatite, thereby reducing the durability of the resulting sealing product. The average particle diameter is preferably 1.0 μm or more and more preferably 2.0 μm or more. When the average particle diameter is more than 10 μm, the particle diameter is too large relative to the diameter of dentinal tubules, which may reduce the initial performance of dentinal tubule sealing. The average particle diameter is preferably 8.0 μm or less and more preferably 6.0 μm or less.

The method for producing the tetracalcium phosphate particles (A) is not particularly limited. Commercially-available tetracalcium phosphate particles may be used as such or may be used after adjustment of their particle diameters by appropriate pulverization. For pulverization, a pulverization apparatus such as a ball mill, a grinder, or a jet mill can be used. Alternatively, the tetracalcium phosphate particles (A) may be obtained by pulverizing commercially-available tetracalcium phosphate particles together with a liquid medium such as an alcohol using a grinder, a ball mill or the like so as to prepare a slurry, and then drying the obtained slurry. Preferred as the pulverization apparatus used in this case is a ball mill. As the material of the pot and balls, there is preferably employed alumina or zirconia. The particles prepared through pulverization as above usually have irregular shapes.

In the curable calcium phosphate composition of the present invention, the content of the tetracalcium phosphate particles (A) is 5 to 75 parts by weight per 100 parts by weight of the total of the tetracalcium phosphate particles (A), the calcium hydrogen phosphate particles (B), and the calcium carbonate particles (C). When the content is less than 5 parts by weight, the cured product has low initial performance and also has low durability. The content of the tetracalcium phosphate particles (A) is preferably 15 parts by weight or more and more preferably 25 parts by weight or more per 100 parts by weight of the above-mentioned total amount. Also when the content of the tetracalcium phosphate particles (A) is more than 75 parts by weight, the cured product has low initial performance and also has low durability. The content of the tetracalcium phosphate particles (A) is preferably 65 parts by weight or less and more preferably 55 parts by weight or less per 100 parts by weight of the above-mentioned total amount.

The calcium hydrogen phosphate particles (B) used in the present invention are not particularly limited. Particles of at least one selected from the group consisting of dibasic calcium phosphate anhydrous (which may be abbreviated as DCPA hereinafter), monobasic calcium phosphate anhydrous, dibasic calcium phosphate dihydrate, and monobasic calcium phosphate monohydrate are preferably used. Among these, particles of dibasic calcium phosphate anhydrous are more preferably used.

The average particle diameter of the calcium hydrogen phosphate particles (B) used in the present invention is preferably 0.1 to 7.5 μm. When the average particle diameter is less than 0.1 μm, a paste obtained by mixing with the water (D) may have too high a viscosity. The average particle diameter is more preferably 0.5 jam or more. When the average particle diameter is more than 7.5 μm, the calcium hydrogen phosphate particles (B) are less soluble in the water (D), which leads to excessive dissolution of the tetracalcium phosphate particles (A) and thereby a high pH of the resulting aqueous solution. This may hinder smooth precipitation of hydroxyapatite, thereby reducing the durability of the cured product. The average particle diameter is more preferably 5.0 μm or less and even more preferably 3.0 μm or less. The average particle diameter of the calcium hydrogen phosphate particles (B) is calculated in the same manner as the average particle diameter of the above-described tetracalcium phosphate particles (A).

The method for producing the calcium hydrogen phosphate particles (B) is not particularly limited. Commercially-available calcium hydrogen phosphate particles may be used as such or may, as in the case of the above-described tetracalcium phosphate particles (A), be used after adjustment of their particle diameters by appropriate pulverization.

In the curable calcium phosphate composition of the present invention, the content of the calcium hydrogen phosphate particles (B) is 10 to 70 parts by weight per 100 parts by weight of the total of the tetracalcium phosphate particles (A), the calcium hydrogen phosphate particles (B), and the calcium carbonate particles (C). When the content is less than 10 parts by weight, curability is insufficient so that a cured product cannot be obtained. The content of the calcium hydrogen phosphate particles (B) is preferably 15 parts by weight or more and more preferably 30 parts by weight or more per 100 parts by weight of the above-mentioned total amount. When the content of the calcium hydrogen phosphate particles (B) is more than 70 parts by weight, the cured product has low initial performance and also has low durability. The content of the calcium hydrogen phosphate particles (B) is preferably 60 parts by weight or less and more preferably 50 parts by weight or less per 100 parts by weight of the above-mentioned total amount.

The calcium carbonate particles (C) constitute an important component for imparting high durability to the calcium phosphate composition with the curability of the composition maintained. When particles of a phosphorus-free calcium compound such as calcium oxide and calcium hydroxide are used instead of the calcium carbonate particles (C), curability is insufficient so that a cured product cannot be obtained.

The average particle diameter of the calcium carbonate particles (C) is preferably 0.1 to 30 μm when the composition of the present invention is used in a bone repair material or in any of dental materials such as a filling restorative material, a lining material, a luting material, a temporary sealing material, a root canal filling material, a temporary cementation material, a coating material, and a sealant. When the average particle diameter is less than 0.1 μm, the calcium carbonate particles (C) are so excessively dissolved that the resulting aqueous solution has a high pH. This may hinder smooth precipitation of hydroxyapatite, thereby reducing the durability of the cured product. The average particle diameter is preferably 0.5 μm or more and more preferably 1 μm or more. When the average particle diameter is more than 30 μm, a paste obtained by mixing with the water (D) may suffer deterioration in quality, such as having insufficient viscosity or having increased roughness. The average particle diameter is preferably 20.0 μm or less and more preferably 15.0 μm or less. The average particle diameter of the calcium carbonate particles (C) is calculated in the same manner as the average particle diameter of the above-described tetracalcium phosphate particles (A).

The average particle diameter of the calcium carbonate particles (C) is preferably 0.1 to 12 μm when the composition of the present invention is used in a dentinal tubule sealing material or the like. When the average particle diameter is less than 0.1 μm, the calcium carbonate particles (C) are so excessively dissolved that the resulting aqueous solution has a high pH. This may hinder smooth precipitation of hydroxyapatite, thereby reducing the durability of the cured product. The average particle diameter is preferably 0.5 μm or more and more preferably 1.0 μm or more. When the average particle diameter is more than 12 μm, the particle diameter is too large relative to the diameter of dentinal tubules, which may reduce the dentinal tubule sealing performance. The average particle diameter is preferably 8.0 μm or less and more preferably 5.0 μm or less.

The method for producing the calcium carbonate particles (C) is not particularly limited. Commercially-available calcium carbonate particles may be used as such or may, as in the case of the above-described tetracalcium phosphate particles (A), be used after adjustment of their particle diameters by appropriate pulverization.

In the curable calcium phosphate composition of the present invention, the content of the calcium carbonate particles (C) is 2 to 50 parts by weight per 100 parts by weight of the total of the tetracalcium phosphate particles (A), the calcium hydrogen phosphate particles (B), and the calcium carbonate particles (C). When the content is less than 2 parts by weight, the cured product has low initial performance and also has low durability. The content of the calcium carbonate particles (C) is preferably 3.5 parts by weight or more and more preferably 5 parts by weight or more per 100 parts by weight of the above-mentioned total amount. When the content of the calcium carbonate particles (C) is more than 50 parts by weight, curability is insufficient so that a cured product cannot be obtained. The content of the calcium carbonate particles (C) is preferably 40 parts by weight or less and more preferably 35 parts by weight or less per 100 parts by weight of the above-mentioned total amount.

The water (D) used in the present invention is an essential component for curing of the curable calcium phosphate composition. The mechanism of the curing of the curable calcium phosphate composition is such that the curing proceeds with accompanying precipitation of hydroxyapatite through reaction of the tetracalcium phosphate particles (A), the calcium hydrogen phosphate particles (B), and the calcium carbonate particles (C) with the water (D).

When the composition of the present invention is used in a bone repair material or in any of dental materials such as a filling restorative material, a lining material, a luting material, a temporary sealing material, a root canal filling material, a temporary cementation material, a coating material, and a sealant, the weight ratio ((A+B+C)/D) of the total of the tetracalcium phosphate particles (A), the calcium hydrogen phosphate particles (B), and the calcium carbonate particles (C) to the water (D) in the paste is preferably 1.8 to 5.0. When the weight ratio ((A+B+C)/D) is less than 1.8, the amounts of the tetracalcium phosphate particles (A), the calcium hydrogen phosphate particles (B), and the calcium carbonate particles (C) in the paste are so excessively small that the durability may be reduced. (In particular, the strength may decrease over time.) The weight ratio ((A+B+C)/D) is more preferably 2.3 or more and even more preferably 2.8 or more. When the weight ratio ((A+B+C)/D) is more than 5.0, the amounts of the tetracalcium phosphate particles (A), the calcium hydrogen phosphate particles (B), and the calcium carbonate particles (C) are so excessively large that the paste may fail to be homogeneously mixed and have deteriorated handling properties. The weight ratio ((A+B+C)/D) is more preferably 4.5 or less and even more preferably 4.0 or less.

When the composition of the present invention is used in a dentinal tubule sealing material or the like, the weight ratio ((A+B+C)/D) of the total of the tetracalcium phosphate particles (A), the calcium hydrogen phosphate particles (B), and the calcium carbonate particles (C) to the water (D) in the paste is preferably 0.5 to 1.8. When the weight ratio ((A+B+C)/D) is less than 0.5, the amounts of the tetracalcium phosphate particles (A), the calcium hydrogen phosphate particles (B), and the calcium carbonate particles (C) in the paste are so excessively small that the initial performance of dentinal tubule sealing may be reduced. The weight ratio ((A+B+C)/D) is more preferably 0.6 or more and even more preferably 0.7 or more. When the weight ratio ((A+B+C)/D) is more than 1.8, the amounts of the tetracalcium phosphate particles (A), the calcium hydrogen phosphate particles (B), and the calcium carbonate particles (C) are so excessively large that proper application of the paste to an affected area may fail, and the handling properties and the acid resistance required of the dentinal tubule sealing material may deteriorate. The weight ratio ((A+B+C)/D) is more preferably 1.7 or less and even more preferably 1.6 or less.

It is preferable for the curable calcium phosphate composition of the present invention to further include an alkali metal phosphate (E), in terms of the initial performance and the durability of the cured product. The alkali metal phosphate (E) used in the present invention is not particularly limited, and examples thereof include disodium hydrogen phosphate, dipotassium hydrogen phosphate, lithium dihydrogen phosphate, sodium dihydrogen phosphate, potassium dihydrogen phosphate, trisodium phosphate, tripotassium phosphate, and hydrates thereof. One or more of these examples are used. In particular, it is preferable for the alkali metal phosphate (E) to be at least one selected from the group consisting of disodium hydrogen phosphate and sodium dihydrogen phosphate in terms of safety and of high availability of a high-purity source material.

The alkali metal phosphate (E) is preferably in the form of particles having an average particle diameter of 1.0 to 20 μm. When the average particle diameter of the alkali metal phosphate (E) is less than 1.0 μm, its dissolution in the composition is so excessively rapid that the concentration of phosphate ions is high. This may cause loss of balance between supply of calcium ions and supply of phosphate ions, resulting in a reduced rate of precipitation of hydroxyapatite. Furthermore, secondary aggregation of the particles of the alkali metal phosphate (E) may occur, thereby reducing their dispersibility with the other particles simultaneously mixed. The average particle diameter of the alkali metal phosphate (E) is more preferably 3.0 μm or more. When the average particle diameter of the alkali metal phosphate (E) is more than 20 μm, the alkali metal phosphate (E) is less soluble in the composition, so the rate of precipitation of hydroxyapatite may become lower. The average particle diameter of the alkali metal phosphate (E) is more preferably 15.0 μm or less. The average particle diameter of the alkali metal phosphate (E) is calculated in the same manner as the average particle diameter of the above-described tetracalcium phosphate particles (A).

In the curable calcium phosphate composition of the present invention, the content of the alkali metal phosphate (E) is 0.5 to 15 parts by weight per 100 parts by weight of the total of the tetracalcium phosphate particles (A), the calcium hydrogen phosphate particles (B), and the calcium carbonate particles (C). When the content is less than 0.5 parts by weight, the addition of the alkali metal phosphate (E) does not improve the performance of the cured product, which means that no effect of the addition is obtained. The content of the alkali metal phosphate (E) is preferably 1 part by weight or more and more preferably 2 parts by weight or more per 100 parts by weight of the above-mentioned total amount. When the content of the alkali metal phosphate (E) is more than 15 parts by weight, the initial performance of the cured product is low. The content of the alkali metal phosphate (E) is preferably 10 parts by weight or less and more preferably 7 parts by weight or less per 100 parts by weight of the above-mentioned total amount.

The method for producing the alkali metal phosphate (E) is not particularly limited. A commercially-available alkali metal phosphate may be used as such or may, as in the case of the above-described tetracalcium phosphate particles (A), be used after adjustment of the particle diameter by appropriate pulverization.

To the extent that the effect of the present invention is not impaired, the curable calcium phosphate composition of the present invention may optionally contain a component other than the tetracalcium phosphate particles (A), the calcium hydrogen phosphate particles (B), the calcium carbonate particles (C), the water (D), and the alkali metal phosphate (E). For example, a fluorine compound, silica particles, a thickener, or an X-ray contrast agent may be contained.

The fluorine compound is not particularly limited, and examples thereof include sodium fluoride, potassium fluoride, ammonium fluoride, lithium fluoride, cesium fluoride, magnesium fluoride, calcium fluoride, strontium fluoride, barium fluoride, copper fluoride, zirconium fluoride, aluminum fluoride, tin fluoride, sodium monofluorophosphate, potassium monofluorophosphate, hydrofluoric acid, titanium sodium fluoride, titanium potassium fluoride, hexylamine hydrofluoride, laurylamine hydrofluoride, glycine hydrofluoride, alanine hydrofluoride, fluorosilanes, and diamine silver fluoride. Among these, sodium fluoride, sodium monofluorophosphate, and tin fluoride are preferably used in view of safety.

The silica particles can prevent aggregation of the powder particles and contribute to keeping the ease of use of the composition. The silica particles are not particularly limited. Their average particle diameter is preferably 0.002 to 2.0 µm. When the average particle diameter of the silica particles is less than 0.002 µm, the paste may have an increased viscosity and hence reduced ease of use. The average particle diameter is preferably 0.003 µm or more and more preferably 0.005 µm or more. When the average particle diameter of the silica particles is more than 2.0 µm, the effect of preventing the aggregation of the powder particles may be reduced. The average particle diameter is preferably 0.5 µm or less and more preferably 0.2 µm or less. The average particle diameter of the silica particles is calculated as follows: a photograph of primary particles dispersed in an epoxy resin is taken by a transmission electron microscope, the diameters of 100 or more primary particles randomly selected from the photograph are measured, and their arithmetic mean is calculated as the average particle diameter.

The thickener is not particularly limited, and an exemplary thickener includes one or more selected from the following polymers: polysaccharides such as carboxymethyl cellulose, sodium carboxymethyl cellulose, hydroxypropyl cellulose, hydroxypropyl methylcellulose, polyvinyl alcohol, polyethylene glycol, polyacrylic acid, polystyrene sulfonic acid, polystyrene sulfonate, polyglutamic acid, polyglutamate, polyaspartic acid, polyaspartate, poly-L-lysine, poly-L-lysine salt, starches other than cellulose, alginic acid, alginate, carrageenan, guar gum, xanthan gum, cellulose gum, hyaluronic acid, hyaluronate, pectin, pectate, chitin, and chitosan; acidic polysaccharide esters such as propylene glycol alginate; and proteins such as collagen, gelatin, and derivatives thereof. In terms of water solubility and viscosity, at least one selected from sodium carboxymethyl cellulose, hydroxypropyl cellulose, hydroxypropyl methylcellulose, alginic acid, alginate, chitosan, polyglutamic acid, and polyglutamate is preferable.

The X-ray contrast agent is not particularly limited, and an exemplary X-ray contrast agent includes one or more selected from barium sulfate, bismuth subcarbonate, bismuth oxide, zirconium oxide, ytterbium fluoride, iodoform, barium apatite, barium titanate, lanthanum glass, barium glass, strontium glass, etc.

Where necessary, there may also be added: a polyhydric alcohol such as glycerin, ethylene glycol, propylene glycol, and diglycerin; a sugar alcohol such as xylitol, sorbitol, and erythritol; a polyether such as polyethylene glycol and polypropylene glycol; or an artificial sweetener such as aspartame, acesulfame potassium, sweet root extract, saccharin, and saccharin sodium. Furthermore, any pharmacologically acceptable agent may be contained. There may be contained: an antibacterial agent typified by cetylpyridinium chloride; an antiseptic agent; an anticancer agent; an antibiotic substance; a blood circulation improving drug such as actosin and PEG1; a growth factor such as bFGF, PDGF, and BMP; cells which promote hard tissue formation, such as osteoblast cells, odontoblast cells, undifferentiated marrow-derived stem cells, embryonic stem (ES) cells, induced pluripotent stem (iPS) cells prepared by dedifferentiation of differentiated cells such as differentiated fibroblast cells through gene transfer, and cells prepared by differentiating those cells.

The curable calcium phosphate composition of the present invention is used in a paste form. The curable calcium phosphate composition of the present invention may be produced as a commodity consisting of separately packaged components. For example, the curable calcium phosphate composition may be produced in the form of a kit including a combination of a powder and a liquid, a paste and another paste, or a liquid and a paste separately packaged.

The method for preparing the powder is not particularly limited. For example, the powder can be obtained by mixing with a grinder, a container-driven mill such as a ball mill, a high-speed rolling mill having a rotary impeller on its bottom, or the like. A high-speed rolling mill is preferably used.

The method for preparing the paste is not particularly limited. For example, the paste can be obtained by mixing with a biaxial kneader, a triaxial kneader, a planetary kneader, or the like.

The method for preparing the liquid is not particularly limited. For example, the liquid can be obtained by mixing with a disperser, a stirrer, or the like.

With the use of the curable calcium phosphate composition of the present invention for biological hard tissue repair, a cured product can bed yielded that undergoes little decrease in strength over time and continues to show resistance to acid over a long period of time in a wet environment such as in a body or an oral cavity; that is, a cured product having excellent durability can be yielded. Hence, the effect of the repair treatment on a biological hard tissue can be maintained over a long period of time. Additionally, the curable calcium phosphate composition of the present invention has good quality in a paste form, has appropriate curability, and has good handling properties. Furthermore, the curable calcium phosphate composition of the present invention is excellent in biocompatibility since it converts to hydroxyapatite in a short period of time and unites with a biological hard tissue in an area to which it is applied.

Thus, the curable calcium phosphate composition of the present invention can be suitably used as a biological hard tissue repair material such as a bone repair material and a dental material. Examples of the bone repair material include a bone filling material and a bone cement. Examples of the dental material include a filling restorative material (used to fill a cavity or a missing part of a tooth structure), a lining material, a luting material, a temporary sealing material, a root canal filling material, a temporary cementation material, a coating material, a sealant, and a dentinal tubule sealing material.

The present invention encompasses embodiments obtainable by combining the above-described features in various manners within the technical scope of the present invention as long as such embodiments exert the effect of the present invention.

EXAMPLES

Hereinafter, the present invention will be described in detail by way of Examples and Comparative Examples. It should be noted that the present invention is not limited to these examples.

[Method for Measuring Average Particle Diameter]

In the present examples, the average particle diameters of the tetracalcium phosphate particles (A), the calcium hydrogen phosphate particles (B), the calcium carbonate particles (C), and the alkali metal phosphate (E) were each determined as a median diameter calculated from the result of particle size distribution measurement using a laser diffraction particle size distribution analyzer ("SALD-2100" manufactured by Shimadzu Corporation).

[Preparation of Each Component]

(1) Preparation of Tetracalcium Phosphate Particles (A)

Tetracalcium phosphate particles manufactured by TAIHEI CHEMICAL INDUSTRIAL CO., LTD. as such were used as the tetracalcium phosphate particles (A) (average particle diameter: 3.2 µm, 5.2 µm, 8.8 µm) in the present examples. Tetracalcium phosphate particles (average particle diameter: 25.8 µm) were prepared in the manner described hereinafter. Commercially-available particles of dibasic calcium phosphate anhydrous (Product No. 1430, manufactured by J.T. Baker Chemical Co.) and calcium carbonate (Product No. 1288, manufactured by J.T. Baker Chemical Co.) were added to water in equimolar amounts, after which stirring was performed for 1 hour, followed by filtration and drying. A cake-like equimolar mixture thus obtained was heated in an electric furnace (FUS 732PB, manufactured by Advantec Toyo Kaisha, Ltd.) at 1500° C. for 24 hours, and then cooled to room temperature in a desiccator, so that tetracalcium phosphate blocks were prepared. The tetracalcium phosphate blocks obtained were coarsely crushed in a mortar and then sieved to remove fine powder particles and tetracalcium phosphate blocks and adjust the particle size to the range of 0.5 to 3 mm. Thus, coarse tetracalcium phosphate was obtained. In a 400 ml milling pot made of alumina ("Type A-3HD pot mill" manufactured by Nikkato Corp.) were put 100 g of the coarse tetracalcium phosphate and 300 g of zirconia balls having a diameter of 20 mm, and the coarse tetracalcium phosphate was milled at a rotation speed of 200 rpm for 2.5 hours. Thus, the tetracalcium phosphate particles were obtained.

Tetracalcium phosphate particles (average particle diameter: 1.1 µm) were prepared in the manner described hereinafter. In a 400 ml milling pot made of alumina ("Type A-3HD pot mill" manufactured by Nikkato Corp.) were put 50 g of commercially-available tetracalcium phosphate particles (manufactured by TAIHEI CHEMICAL INDUSTRIAL CO., LTD. and having an average particle diameter of 5.2 µm), 120 g of 95% ethanol ("Ethanol (95)" manufactured by Wako Pure Chemical Industries, Ltd.), and 240 g of zirconia balls having a diameter of 10 mm. Wet milling was performed at a rotation speed of 120 rpm for 24 hours to obtain a slurry, from which the ethanol was distilled off using a rotary evaporator and which was then dried at 60° C. for 6 hours and further vacuum-dried at 60° C. for 24 hours. Thus, the tetracalcium phosphate particles were obtained.

(2) Preparation of Calcium Hydrogen Phosphate Particles (B)

Particles of dibasic calcium phosphate anhydrous (average particle diameter: 1.1 µm) used as one example of the calcium hydrogen phosphate particles (B) in the present examples were obtained as follows: 50 g of commercially-available particles of dibasic calcium phosphate anhydrous (manufactured by TAIHEI CHEMICAL INDUSTRIAL CO., LTD. and having an average particle diameter of 10.1 µm), 120 g of 95% ethanol ("Ethanol (95)" manufactured by Wako Pure Chemical Industries, Ltd.), and 240 g of zirconia balls having a diameter of 10 mm were put into a 400 ml milling pot made of alumina ("Type A-3HD pot mill" manufactured by Nikkato Corp.), and wet milling was performed at a rotation speed of 120 rpm for 24 hours to obtain a slurry, from which the ethanol was distilled off using a rotary evaporator and which was then dried at 60° C. for 6 hours and further vacuum-dried at 60° C. for 24 hours.

Particles of dibasic calcium phosphate anhydrous (average particle diameter: 5.0 µm) were obtained as follows: 50 g of commercially-available particles of dibasic calcium phosphate anhydrous (manufactured by Wako Pure Chemical Industries, Ltd. and having an average particle diameter of 10.2 µm), 240 g of 95% ethanol, and 480 g of zirconia balls having a diameter of 10 mm were put into a 1000 ml milling pot made of alumina ("HD-B-104 pot mill" manufactured by Nikkato Corp.), and wet vibratory milling was performed at a rotation speed of 1500 rpm for 7 hours to obtain a slurry, from which the ethanol was distilled off using a rotary evaporator and which was then dried at 60° C. for 6 hours and further vacuum-dried at 60° C. for 24 hours.

Particles of dibasic calcium phosphate anhydrous (average particle diameter: 0.3 µm) were obtained as follows: 50 g of commercially-available particles of dibasic calcium phosphate anhydrous (manufactured by Wako Pure Chemical Industries, Ltd. and having an average particle diameter of 10.2 µm), 240 g of 95% ethanol, and 480 g of zirconia balls having a diameter of 10 mm were put into a 1000 ml milling pot made of alumina ("HD-B-104 pot mill" manufactured by Nikkato Corp.), and wet vibratory milling was performed at a rotation speed of 1500 rpm for 40 hours to obtain a slurry, from which the ethanol was distilled off using a rotary evaporator and which was then dried at 60° C. for 6 hours and further vacuum-dried at 60° C. for 24 hours.

(3) Preparation of Calcium Carbonate Particles (C)

Calcium carbonate particles manufactured by YABASHI INDUSTRIES CO., LTD. as such were used as calcium carbonate particles (average particle diameter: 2.6 μm) in the present examples.

Calcium carbonate particles manufactured by Konoshima Chemical Co., Ltd. as such were used as calcium carbonate particles (average particle diameter: 25.4 μm) in the present examples.

Calcium carbonate particles (average particle diameter: 10.2 μm) were obtained as follows: 50 g of commercially-available calcium carbonate particles (manufactured by Konoshima Chemical Co., Ltd. and having an average particle diameter of 25.4 μm), 240 g of 95% ethanol, and 480 g of zirconia balls having a diameter of 10 mm were put into a 1000 ml milling pot made of alumina ("HD-B-104 pot mill" manufactured by Nikkato Corp.), and wet vibratory milling was performed at a rotation speed of 1500 rpm for 5 hours to obtain a slurry, from which the ethanol was distilled off using a rotary evaporator and which was then dried at 60° C. for 6 hours and further vacuum-dried at 60° C. for 24 hours.

Calcium carbonate particles (average particle diameter: 0.5 μm) used in the present examples were obtained as follows: 50 g of commercially-available calcium carbonate particles (manufactured by Konoshima Chemical Co., Ltd. and having an average particle diameter of 25.4 μm), 240 g of 95% ethanol, and 480 g of zirconia balls having a diameter of 10 mm were put into a 1000 ml milling pot made of alumina ("HD-B-104 pot mill" manufactured by Nikkato Corp.), and wet vibratory milling was performed at a rotation speed of 1500 rpm for 35 hours to obtain a slurry, from which the ethanol was distilled off using a rotary evaporator and which was then dried at 60° C. for 6 hours and further vacuum-dried at 60° C. for 24 hours.

(4) Preparation of Alkali Metal Phosphate (E)

Disodium hydrogen phosphate particles (average particle diameter: 5.2 μm) used as one example of the alkali metal phosphate (E) in the present examples were obtained by processing commercially-available disodium hydrogen phosphate (manufactured by Wako Pure Chemical Industries, Ltd.) once by Nano Jetmizer (NJ-100, manufactured by Aisin Nanotechnology) under the following conditions: source material supply pressure=0.7 MPa, crushing pressure=0.7 MPa, through put=8 kg/hr).

Calcium hydroxide, calcium oxide, calcium silicate, calcium nitrate, and calcium oxalate manufactured by Wako Pure Chemical Industries, Ltd. as such were used as those in Comparative Examples.

[Preparation of Powder (X)]

The tetracalcium phosphate particles (A), the calcium hydrogen phosphate particles (B), the calcium carbonate particles (C), and optionally the alkali metal phosphate (E), which were weighed to give compositions shown in Tables 1 to 3 and 5 to 7, were put into a high-speed rotating mill ("SM-1" manufactured by AS ONE Corporation) and mixed at a rotation speed of 1000 rpm for 3 minutes to obtain powders (X).

[Preparation of Liquid (Y)]

Liquids (Y) in which was used the alkali metal phosphate (E) were obtained by putting in a beaker the alkali metal phosphate (E) and the water (D) which were weighed to give compositions shown in Table 3 and 7 and stirring them with a magnetic stirrer for 1 hour.

[Preparation of Paste (V)]

The tetracalcium phosphate particles (A), the calcium carbonate particles (C), the water (D), and optionally the alkali metal phosphate (E), which were weighed to give compositions shown in Table 4, were put in a universal mixing stirrer ("STM-08" manufactured by Dalton Co., Ltd.) and mixed at a rotation speed of 130 rpm and a revolution speed of 37 rpm for 60 minutes to obtain pastes (V).

[Preparation of Paste (W)]

The calcium hydrogen phosphate particles (B), the water (D), and optionally the alkali metal phosphate (E), which were weighed to give compositions shown in Table 4, were put in a universal mixing stirrer ("STM-08" manufactured by Dalton Co., Ltd.) and mixed at a rotation speed of 130 rpm and a revolution speed of 37 rpm for 60 minutes to obtain pastes (W).

[Compressive Strength Test]

(1) Preparation of Sample for Compressive Strength Measurement

A paste of each dental curable calcium phosphate composition was loaded in a stainless steel split mold with a diameter of 6 mm and a depth of 3 mm which was placed on a flat, smooth glass sheet, with careful attention to avoid inclusion of gas. The composition paste was compressed from above by a flat, smooth glass sheet into a cylindrical form (n=5). Thereafter, the paste was incubated at a temperature of 37° C. and a relative humidity of 100% for 24 hours, after which the cured product was removed out from the mold, immersed in 150 ml of 37° C. distilled water, and left for additional 24 hours (the resulting product is referred to as an "initial sample"). In order to evaluate deterioration over time, the initial sample was immersed in 150 ml of 70° C. distilled water, and left for 7 days (the resulting product is referred to as a "70° C./7-day-treated sample").

(2) Measurement of Compressive Strength

According to the method specified in JIS T 6609-1 and using a mechanical strength analyzer ("AG-1 100 kN" manufactured by Shimadzu Corporation), the compressive strength (MPa) of each of the initial sample and the 70° C./7-day-treated sample prepared in (1) was measured by applying a load in the axial direction of the cylindrical cured product at a rate of 0.75 mm/min (n=5). In the tables below, "Initial compressive strength" refers to the compressive strength of the initial sample and "Post-70° C./1-week treatment compressive strength" refers to the compressive strength of the 70° C./7-day-treated sample. The decrease ratio of compressive strength was calculated by the following formula.

Decrease ratio of compressive strength (%)=100−{[Post-70° C./1-week treatment compressive strength/Initial compressive strength]×100}

[Test of Handling Properties (I)]

(1) Handling Properties

The powders composed as shown in Tables 1 to 3 were each accurately weighed to 0.1 g, the liquids composed as shown in Tables 1 to 3 were added to the corresponding powders so as to give powder-to-liquid weight ratios shown in Tables 1 to 3, and the powders and the liquids were mixed on mixing pads (85×115 mm) to prepare pastes. The handling properties were evaluated according to the following criteria based on the mixing time and the paste quality.

(2) Evaluation Criteria of Handling Properties

A: The compatibility between the powder and the liquid during mixing is good, and a paste can be obtained by mixing with a dental mixing rod for 30 seconds. The obtained paste has good stretchability.

B: The compatibility between the powder and the liquid during mixing is slightly poor; however, a paste can be obtained by mixing with a dental mixing rod for 30 seconds. The stretchability of the paste is somewhat poorer than that in the case of A.

C: The compatibility between the powder and the liquid during mixing is poor. Obtaining a paste requires mixing with a dental mixing rod for 60 seconds. The roughness of the paste is somewhat large.

D: The compatibility between the powder and the liquid during mixing is poor. Obtaining a paste requires mixing with a dental mixing rod for more than 60 seconds or mixing is not possible. Even if mixing is possible, the resulting paste has poor stretchability, and cures on a mixing pad within 2 minutes, so that sufficient working time cannot be secured.

A to C correspond to the levels acceptable for practical use.

[Test of Dentinal Tubule Sealing Ratio]

(1) Preparation of Disc of Bovine Tooth

The buccal center of a healthy bovine incisor was ground with waterproof abrasive paper No. 80 and then No. 1000 to have the dentin exposed and form the bovine tooth into a disc having a diameter of about 7 mm and a thickness of 2 mm. The ground surface of the bovine tooth was further ground with wrapping films No. 1200, No. 3000, and then No. 8000 (manufactured by Sumitomo 3M). Next, the bovine tooth was immersed in a solution prepared by five-fold dilution of a 0.5 M EDTA solution (manufactured by Wako Pure Chemical Industries, Ltd.) for 30 minutes, then washed with water for 60 seconds, subjected to a 10% sodium hypochlorite solution (Neo Cleaner "SEKINE" manufactured by NEO DENTAL CHEMICAL PRODUCTS CO., LTD.) for 60 seconds, and finally washed with water for 60 seconds.

(2) Preparation of Artificial Saliva

Sodium chloride (8.77 g, 150 mmol), potassium dihydrogen phosphate (122 mg, 0.9 mmol), calcium chloride (166 mg, 1.5 mmol), and Hepes (4.77 g, 20 mmol) were each weighed into a weighing dish, and sequentially added to about 800 ml of distilled water held in a 2000 ml beaker under stirring. After confirmation of complete dissolution of the solutes, a 10% aqueous sodium hydroxide solution was added dropwise with simultaneous measurement of the acidity of the solution by a pH meter (F55, manufactured by HORIBA, Ltd.) to adjust the pH to 7.0.

(3) Sealing of Dentinal Tubules and Acid Immersion

A paste of each dentinal tubule sealing material weighed to 0.1 g was put onto the buccal dentin surface of the disc of bovine tooth obtained in (1), and rubbed over a 5-mm-diameter area of the central portion of the treated dentin surface using Microbrush Regular (manufactured by Microbrush Co.) for 30 seconds. Thereafter, the paste of the dentinal tubule sealing material on the surface of the disc of bovine tooth was removed with distilled water, and the disc of bovine tooth was immersed in the artificial saliva obtained in (2) at 37° C. for 24 hours to obtain a test piece (A) for SEM observation. For evaluation of the post-acid immersion dentinal tubule sealing ratio, the disc of bovine tooth treated with the above dentinal tubule sealing material and immersed in the artificial saliva at 37° C. for 24 hours was horizontally immersed in 30 mL of a 0.1 M lactic acid buffer solution (pH=4.75) held in a separate container at 37° C. for 10 minutes, with the surface treated with the dentinal tubule sealing material facing upward. Thereafter, the disc of bovine tooth was washed with distilled water, and then immersed in the artificial saliva at 37° C. The acid immersion was performed in a once per day cycle. This operation was repeated for 14 days to obtain a test piece (B) for SEM observation.

(4) SEM Observation

The test pieces (A) and (B) obtained in (3) were dried at room temperature under reduced pressure for 1 hour and subjected to metal vapor deposition, after which the surfaces treated with the dentinal tubule sealing material were each observed at three arbitrarily-selected points using a scanning electron microscope (S-3500N, manufactured by Hitachi High-Technologies Corporation) at a magnification of 3000 times. The dentinal tubule sealing ratio in each observation field of view was calculated according to the formula given below, and the values obtained for the three points were averaged. The number of tests performed was 5 (n=5), and the values obtained through all the tests were averaged, and the average was determined as the dentinal tubule sealing ratio. The dentinal tubule sealing ratio for the test piece (A) was shown as "Dentinal tubule sealing ratio (initial)" in the tables below. The dentinal tubule sealing ratio for the test piece (B) was shown as "Dentinal tubule sealing ratio (post-acid immersion)" in the tables below.

$$\text{Dentinal tubule sealing ratio (\%)} = \{(\text{Number of sealed dentinal tubules})/(\text{Number of total dentinal tubules})\} \times 100$$

In the tables below, the values of the decrease ratio (%) of the dentinal tubule sealing ratio are those calculated by the following formula.

$$\text{Decrease ratio (\%) of dentinal tubule sealing ratio} = 100 - \{[\text{Dentinal tubule sealing ratio (post-acid immersion)}/\text{Dentinal tubule sealing ratio (initial)}] \times 100\}$$

[Test of Handling Properties (II)]

(1) Handling Properties

The pastes composed as shown in Tables 5 to 7 were each accurately weighed to 0.1 g, and applied to artificial teeth of a dental cast using Microbrush Regular (Microbrush Co.). The performance in terms of the application was evaluated according to the following criteria.

(2) Evaluation Criteria of Handling Properties

A: Application can easily be achieved with Microbrush Regular within 30 seconds per tooth. Additionally, the paste is securely held on tooth surfaces without running down during application.

B: Application can be achieved with Microbrush Regular within 30 seconds per tooth. However, the paste has poor stretchability and is somewhat difficult to apply, or the paste is somewhat soft and somewhat likely to run down during application.

C: The paste is hard so that it takes more than 30 seconds but 60 seconds or less per tooth to apply the paste with Microbrush Regular. Or the paste is soft and likely to run down during application.

D: The paste is so excessively hard that application with Microbrush Regular requires more than 60 seconds per tooth. Or the paste is so excessively soft that the paste rapidly runs down and cannot be applied.

A to C correspond to the levels acceptable for practical use.

Examples 1 to 29

Curable calcium phosphate compositions composed as shown in Tables 1 to 4 were prepared by the procedures described above, and were evaluated for the initial compressive strength, the post-70° C./7-day treatment compressive strength, and the handling properties (I). The evaluation results obtained are collectively shown in Tables 1 to 4.

Examples 30 to 56

Curable calcium phosphate compositions (pasty dentinal tubule sealing materials) composed as shown in Tables 5 to 7 were prepared by the procedures described above, and were evaluated for the initial dentinal tubule sealing ratio, the post-acid immersion dentinal tubule sealing ratio, and the handling properties (II). The evaluation results obtained are collectively shown in Tables 5 to 7.

Comparative Examples 1 to 26

Curable calcium phosphate compositions composed as shown in Tables 8 to 10 were prepared by the same procedures as those in Examples above, and were evaluated for the initial compressive strength, the post-70° C./7-day treatment compressive strength, the handling properties (I), the initial dentinal tubule sealing ratio, the post-acid immersion dentinal tubule sealing ratio, and the handling properties (II). The evaluation results obtained are collectively shown in Tables 8 to 10.

TABLE 1

|  |  |  |  | Example 1 | Example 2 | Example 3 | Example 4 | Example 5 | Example 6 | Example 7 | Example 8 | Example 9 |
|---|---|---|---|---|---|---|---|---|---|---|---|---|
| Powder (X) | A | TTCP (D50: 3.2 μm) | (parts by weight) | | | | | | | | | |
| | | TTCP (D50: 8.8 μm) | (parts by weight) | 41.0 | 50.0 | 30.0 | 47.0 | 33.5 | 60.0 | 20.0 | 65.0 | 45.0 |
| | | TTCP (D50: 25.8 μm) | (parts by weight) | | | | | | | | | |
| | B | DCPA (D50: 0.3 μm) | (parts by weight) | | | | | | | | | |
| | | DCPA (D50: 1.1 μm) | (parts by weight) | 41.0 | 35.0 | 45.0 | 46.0 | 33.5 | 25.0 | 55.0 | 31.0 | 15.0 |
| | | DCPA (D50: 5.0 μm) | (parts by weight) | | | | | | | | | |
| | C | Calcium carbonate (D50: 0.5 μm) | (parts by weight) | | | | | | | | | |
| | | Calcium carbonate (D50: 2.6 μm) | (parts by weight) | 18.0 | 15.0 | 25.0 | 7.0 | 33.0 | 15.0 | 25.0 | 4.0 | 40.0 |
| | | Calcium carbonate (D50: 25.4 μm) | (parts by weight) | | | | | | | | | |
| | E | $Na_2HPO_4$ (D50: 5.2 μm) | (parts by weight) | | | | | | | | | |
| Total | | | (parts by weight) | 100.0 | 100.0 | 100.0 | 100.0 | 100.0 | 100.0 | 100.0 | 100.0 | 100.0 |
| Liquid (Y) | E | $Na_2HPO_4$ (D50: 5.2 μm) | (parts by weight) | | | | | | | | | |
| | D | Water | (parts by weight) | 100.0 | 100.0 | 100.0 | 100.0 | 100.0 | 100.0 | 100.0 | 100.0 | 100.0 |
| Total | | | (parts by weight) | 100.0 | 100.0 | 100.0 | 100.0 | 100.0 | 100.0 | 100.0 | 100.0 | 100.0 |
| Powder-to-liquid ratio (X/Y) | | | | 3.5 | 3.5 | 3.5 | 3.5 | 3.5 | 3.5 | 3.5 | 3.5 | 3.5 |
| Weight ratio ((A + B + C)/D) | | | | 3.5 | 3.5 | 3.5 | 3.5 | 3.5 | 3.5 | 3.5 | 3.5 | 3.5 |
| Handling properties (I) | | | | B | B | B | B | B | B | B | B | B |
| Initial compressive strength | | | (MPa) | 55.3 | 52.6 | 53.3 | 50.8 | 48.8 | 45.1 | 46.4 | 44.9 | 42.2 |
| Post-70° C./1-week treatment compressive strength | | | (MPa) | 42.8 | 40.8 | 39.1 | 37.9 | 37.6 | 31.8 | 33.4 | 32.2 | 30.7 |
| Decrease ratio of compressive strength | | | (%) | 22.6 | 22.4 | 26.6 | 25.4 | 23.0 | 29.5 | 28.0 | 28.3 | 27.3 |
| Content of A per 100 parts by weight of total of A + B + C | | | (parts by weight) | 41.0 | 50.0 | 30.0 | 47.0 | 33.5 | 60.0 | 20.0 | 65.0 | 45.0 |
| Content of B per 100 parts by weight of total of A + B + C | | | (parts by weight) | 41.0 | 35.0 | 45.0 | 46.0 | 33.5 | 25.0 | 55.0 | 31.0 | 15.0 |
| Content of C per 100 parts by weight of total of A + B + C | | | (parts by weight) | 18.0 | 15.0 | 25.0 | 7.0 | 33.0 | 15.0 | 25.0 | 4.0 | 40.0 |
| Content of E per 100 parts by weight of total of A + B + C | | | (parts by weight) | 0 | 0 | 0 | 0 | 0 | 0 | 0 | 0 | 0 |

TABLE 2

| | | | | Example 10 | Example 11 | Example 12 | Example 13 | Example 14 |
|---|---|---|---|---|---|---|---|---|
| Powder (X) | A | TTCP (D50: 3.2 μm) | (parts by weight) | | | | | 41.0 |
| | | TTCP (D50: 8.8 μm) | (parts by weight) | 10.0 | 70.0 | 75.0 | 5.0 | |
| | | TTCP (D50: 25.8 μm) | (parts by weight) | | | | | |
| | B | DCPA (D50: 0.3 μm) | (parts by weight) | | | | | |
| | | DCPA (D50: 1.1 μm) | (parts by weight) | 65.0 | 10.0 | 23.0 | 45.0 | 41.0 |
| | | DCPA (D50: 5.0 μm) | (parts by weight) | | | | | |
| | C | Calcium carbonate (D50: 0.5 μm) | (parts by weight) | | | | | |
| | | Calcium carbonate (D50: 2.6 μm) | (parts by weight) | 25.0 | 20.0 | 2.0 | 50.0 | 18.0 |
| | | Calcium carbonate (D50: 25.4 μm) | (parts by weight) | | | | | |
| | E | $Na_2HPO_4$ (D50: 5.2 μm) | (parts by weight) | | | | | |
| Total | | | (parts by weight) | 100.0 | 100.0 | 100.0 | 100.0 | 100.0 |
| Liquid (Y) | E | $Na_2HPO_4$ (D50: 5.2 μm) | (parts by weight) | | | | | |
| | D | Water | (parts by weight) | 100.0 | 100.0 | 100.0 | 100.0 | 100.0 |
| Total | | | (parts by weight) | 100.0 | 100.0 | 100.0 | 100.0 | 100.0 |
| Powder-to-liquid ratio (X/Y) | | | | 3.5 | 3.5 | 3.5 | 3.5 | 3.5 |
| Weight ratio ((A + B + C)/D) | | | | 3.5 | 3.5 | 3.5 | 3.5 | 3.5 |
| Handling properties (I) | | | | B | B | B | B | B |
| Initial compressive strength | | | (MPa) | 36.4 | 38.1 | 37.5 | 35.5 | 46.6 |
| Post-70° C./1-week treatment compressive strength | | | (MPa) | 24.6 | 24.6 | 25.1 | 23.7 | 35.9 |
| Decrease ratio of compressive strength | | | (%) | 32.4 | 35.4 | 33.1 | 33.2 | 23.0 |
| Content of A per 100 parts by weight of total of A + B + C | | | (parts by weight) | 10.0 | 70.0 | 75.0 | 5.0 | 41.0 |
| Content of B per 100 parts by weight of total of A + B + C | | | (parts by weight) | 65.0 | 10.0 | 23.0 | 45.0 | 41.0 |
| Content of C per 100 parts by weight of total of A + B + C | | | (parts by weight) | 25.0 | 20.0 | 2.0 | 50.0 | 18.0 |
| Content of E per 100 parts by weight of total of A + B + C | | | (parts by weight) | 0 | 0 | 0 | 0 | 0 |

| | | | | Example 15 | Example 16 | Example 17 | Example 18 | Example 19 |
|---|---|---|---|---|---|---|---|---|
| Powder (X) | A | TTCP (D50: 3.2 μm) | (parts by weight) | | | | | |
| | | TTCP (D50: 8.8 μm) | (parts by weight) | | 41.0 | 41.0 | 41.0 | 41.0 |
| | | TTCP (D50: 25.8 μm) | (parts by weight) | 41.0 | | | | |
| | B | DCPA (D50: 0.3 μm) | (parts by weight) | | 41.0 | | | |
| | | DCPA (D50: 1.1 μm) | (parts by weight) | 41.0 | | | 41.0 | 41.0 |
| | | DCPA (D50: 5.0 μm) | (parts by weight) | | | 41.0 | | |
| | C | Calcium carbonate (D50: 0.5 μm) | (parts by weight) | | | | 18.0 | |
| | | Calcium carbonate (D50: 2.6 μm) | (parts by weight) | 18.0 | 18.0 | 18.0 | | |
| | | Calcium carbonate (D50: 25.4 μm) | (parts by weight) | | | | | 18.0 |
| | E | $Na_2HPO_4$ (D50: 5.2 μm) | (parts by weight) | | | | | |
| Total | | | (parts by weight) | 100.0 | 100.0 | 100.0 | 100.0 | 100.0 |

TABLE 2-continued

| | | | | | | | | |
|---|---|---|---|---|---|---|---|---|
| Liquid (Y) | E | Na$_2$HPO$_4$ (D50: 5.2 μm) | (parts by weight) | | | | | |
| | D | Water | (parts by weight) | 100.0 | 100.0 | 100.0 | 100.0 | 100.0 |
| Total | | | (parts by weight) | 100.0 | 100.0 | 100.0 | 100.0 | 100.0 |
| Powder-to-liquid ratio (X/Y) | | | | 3.5 | 3.5 | 3.5 | 3.5 | 3.5 |
| Weight ratio ((A + B + C)/D) | | | | 3.5 | 3.5 | 3.5 | 3.5 | 3.5 |
| Handling properties (I) | | | | C | C | B | B | C |
| Initial compressive strength | | | (MPa) | 57.6 | 50.9 | 45.7 | 44.2 | 55.8 |
| Post-70° C./1-week treatment compressive strength | | | (MPa) | 43.2 | 39.4 | 33.4 | 33.6 | 40.9 |
| Decrease ratio of compressive strength | | | (%) | 25.0 | 22.6 | 26.9 | 24.0 | 26.7 |
| Content of A per 100 parts by weight of total of A + B + C | | | (parts by weight) | 41.0 | 41.0 | 41.0 | 41.0 | 41.0 |
| Content of B per 100 parts by weight of total of A + B + C | | | (parts by weight) | 41.0 | 41.0 | 41.0 | 41.0 | 41.0 |
| Content of C per 100 parts by weight of total of A + B + C | | | (parts by weight) | 18.0 | 18.0 | 18.0 | 18.0 | 18.0 |
| Content of E per 100 parts by weight of total of A + B + C | | | (parts by weight) | 0 | 0 | 0 | 0 | 0 |

TABLE 3

| | | | | Example 20 | Example 21 | Example 22 | Example 23 | Example 24 | Example 25 | Example 26 | Example 27 |
|---|---|---|---|---|---|---|---|---|---|---|---|
| Powder (X) | A | TTCP (D50: 3.2 μm) | (parts by weight) | | | | | | | | |
| | | TTCP (D50: 8.8 μm) | (parts by weight) | 41.0 | 41.0 | 38.0 | 41.0 | 36.0 | 41.0 | 41.0 | 41.0 |
| | | TTCP (D50: 25.8 μm) | (parts by weight) | | | | | | | | |
| | B | DCPA (D50: 0.3 μm) | (parts by weight) | | | | | | | | |
| | | DCPA (D50: 1.1 μm) | (parts by weight) | 41.0 | 41.0 | 38.0 | 41.0 | 36.0 | 41.0 | 41.0 | 41.0 |
| | | DCPA (D50: 5.0 μm) | (parts by weight) | | | | | | | | |
| | C | Calcium carbonate (D50: 0.5 μm) | (parts by weight) | | | | | | | | |
| | | Calcium carbonate (D50: 2.6 μm) | (parts by weight) | 18.0 | 18.0 | 16.0 | 18.0 | 15.0 | 18.0 | 18.0 | 18.0 |
| | | Calcium carbonate (D50: 25.4 μm) | (parts by weight) | | | | | | | | |
| | E | Na$_2$HPO$_4$ (D50: 5.2 μm) | (parts by weight) | | | 8.0 | | 13.0 | | | |
| Total | | | (parts by weight) | 100.0 | 100.0 | 100.0 | 100.0 | 100.0 | 100.0 | 100.0 | 100.0 |
| Liquid (Y) | E | Na$_2$HPO$_4$ (D50: 5.2 μm) | (parts by weight) | 12.0 | 4.2 | | 2.8 | | | | |
| | D | Water | (parts by weight) | 88.0 | 95.8 | 100.0 | 97.2 | 100.0 | 100.0 | 100.0 | 100.0 |
| Total | | | (parts by weight) | 100.0 | 100.0 | 100.0 | 100.0 | 100.0 | 100.0 | 100.0 | 100.0 |
| Powder-to-liquid ratio (X/Y) | | | | 3.5 | 3.5 | 3.5 | 3.5 | 3.5 | 1.8 | 2.3 | 4.5 |
| Weight ratio ((A + B + C)/D) | | | | 4.0 | 3.7 | 3.2 | 3.6 | 3.0 | 1.8 | 2.3 | 4.5 |
| Handling properties (I) | | | | B | B | B | B | B | A | A | C |
| Initial compressive strength | | | (MPa) | 85.3 | 78.9 | 80.6 | 70.6 | 66.4 | 36.8 | 43.9 | 61.3 |
| Post-70° C./1-week treatment compressive strength | | | (MPa) | 73.4 | 65.2 | 65.9 | 56.7 | 52.5 | 27.1 | 33.8 | 49.5 |
| Decrease ratio of compressive strength | | | (%) | 14.0 | 17.4 | 18.2 | 19.7 | 20.9 | 26.4 | 23.0 | 19.2 |
| Content of A per 100 parts by weight of total of A + B + C | | | (parts by weight) | 41.0 | 41.0 | 41.3 | 41.0 | 41.4 | 41.0 | 41.0 | 41.0 |
| Content of B per 100 parts by weight of total of A + B + C | | | (parts by weight) | 41.0 | 41.0 | 41.3 | 41.0 | 41.4 | 41.0 | 41.0 | 41.0 |
| Content of C per 100 parts by weight of total of A + B + C | | | (parts by weight) | 18.0 | 18.0 | 17.4 | 18.0 | 17.2 | 18.0 | 18.0 | 18.0 |
| Content of E per 100 parts by weight of total of A + B + C | | | (parts by weight) | 3.4 | 1.2 | 8.7 | 0.8 | 14.9 | 0 | 0 | 0 |

TABLE 4

|  |  |  |  | Example 28 | Example 29 |
|---|---|---|---|---|---|
| Paste (V) | A | TTCP (D50: 8.8 μm) | (parts by weight) | 35.7 | 35.7 |
|  | C | Calcium carbonate (D50: 2.6 μm) | (parts by weight) | 35.7 | 35.7 |
|  | D | Water | (parts by weight) | 28.6 | 25.8 |
|  | E | $Na_2HPO_4$ (D50: 5.2 μm) | (parts by weight) |  | 2.8 |
|  |  | Total | (parts by weight) | 100.0 | 100.0 |
| Paste (W) | B | DCPA (D50: 1.1 μm) | (parts by weight) | 71.4 | 71.4 |
|  | D | Water | (parts by weight) | 28.6 | 25.8 |
|  | E | $Na_2HPO_4$ (D50: 5.2 μm) | (parts by weight) |  | 2.8 |
|  |  | Total | (parts by weight) | 100.0 | 100.0 |
| Paste-to-paste weight ratio (V/W) |  |  |  | 1.0 | 1.0 |
| Weight ratio ((A + B + C)/D) |  |  |  | 2.5 | 2.8 |
| Initial compressive strength |  |  | (MPa) | 42.7 | 72.3 |
| Post-70° C./1-week treatment compressive strength |  |  | (MPa) | 31.8 | 59.7 |
| Decrease ratio of compressive strength |  |  | (%) | 25.5 | 17.4 |
| Content of A per 100 parts by weight of total of A + B + C | | | (parts by weight) | 25.0 | 25.0 |
| Content of B per 100 parts by weight of total of A + B + C | | | (parts by weight) | 50.0 | 50.0 |
| Content of C per 100 parts by weight of total of A + B + C | | | (parts by weight) | 25.0 | 25.0 |
| Content of E per 100 parts by weight of total of A + B + C | | | (parts by weight) | 0 | 3.9 |

TABLE 5

|  |  |  |  | Example 30 | Example 31 | Example 32 | Example 33 | Example 34 | Example 35 | Example 36 | Example 37 | Example 38 |
|---|---|---|---|---|---|---|---|---|---|---|---|---|
| Powder (X) | A | TTCP (D50: 1.1 μm) | (parts by weight) |  |  |  |  |  |  |  |  |  |
|  |  | TTCP (D50: 5.2 μm) | (parts by weight) | 41.0 | 50.0 | 30.0 | 47.0 | 33.5 | 60.0 | 20.0 | 65.0 | 40.0 |
|  |  | TTCP (D50: 8.8 μm) | (parts by weight) |  |  |  |  |  |  |  |  |  |
|  | B | DCPA (D50: 0.3 μm) | (parts by weight) |  |  |  |  |  |  |  |  |  |
|  |  | DCPA (D50: 1.1 μm) | (parts by weight) | 41.0 | 35.0 | 45.0 | 46.0 | 33.5 | 25.0 | 55.0 | 31.0 | 20.0 |
|  |  | DCPA (D50: 5.0 μm) | (parts by weight) |  |  |  |  |  |  |  |  |  |
|  | C | Calcium carbonate (D50: 0.5 μm) | (parts by weight) |  |  |  |  |  |  |  |  |  |
|  |  | Calcium carbonate (D50: 2.6 μm) | (parts by weight) | 18.0 | 15.0 | 25.0 | 7.0 | 33.0 | 15.0 | 25.0 | 4.0 | 40.0 |
|  |  | Calcium carbonate (D50: 10.2 μm) | (parts by weight) |  |  |  |  |  |  |  |  |  |
|  | E | $Na_2HPO_4$ (D50: 5.2 μm) | (parts by weight) |  |  |  |  |  |  |  |  |  |
| Total |  |  | (parts by weight) | 100.0 | 100.0 | 100.0 | 100.0 | 100.0 | 100.0 | 100.0 | 100.0 | 100.0 |
| Liquid (Y) | E | $Na_2HPO_4$ (D50: 5.2 μm) | (parts by weight) |  |  |  |  |  |  |  |  |  |
|  | D | Water | (parts by weight) | 100.0 | 100.0 | 100.0 | 100.0 | 100.0 | 100.0 | 100.0 | 100.0 | 100.0 |
| Total |  |  | (parts by weight) | 100.0 | 100.0 | 100.0 | 100.0 | 100.0 | 100.0 | 100.0 | 100.0 | 100.0 |
| Powder-to-liquid ratio (X/Y) |  |  |  | 1.2 | 1.2 | 1.2 | 1.2 | 1.2 | 1.2 | 1.2 | 1.2 | 1.2 |
| Weight ratio ((A + B + C)/D) |  |  |  | 1.2 | 1.2 | 1.2 | 1.2 | 1.2 | 1.2 | 1.2 | 1.2 | 1.2 |
| Dentinal tubule sealing ratio (initial) |  |  | (%) | 100 | 100 | 100 | 100 | 100 | 100 | 100 | 100 | 100 |
| Dentinal tubule sealing ratio (post-acid immersion) |  |  | (%) | 80.2 | 78.6 | 79.5 | 80.9 | 81.5 | 75.4 | 71.5 | 72.9 | 73.4 |
| Decrease ratio of dentinal tubule sealing ratio |  |  | (%) | 19.8 | 21.4 | 20.5 | 19.1 | 18.5 | 24.6 | 28.5 | 27.1 | 26.6 |
| Handling properties (II) |  |  |  | A | A | A | A | A | A | A | A | A |
| Content of A per 100 parts by weight of total of A + B + C |  |  | (parts by weight) | 41.0 | 50.0 | 30.0 | 47.0 | 33.5 | 60.0 | 20.0 | 65.0 | 40.0 |
| Content of B per 100 parts by weight of total of A + B + C |  |  | (parts by weight) | 41.0 | 35.0 | 45.0 | 46.0 | 33.5 | 25.0 | 55.0 | 31.0 | 20.0 |
| Content of C per 100 parts by weight of total of A + B + C |  |  | (parts by weight) | 18.0 | 15.0 | 25.0 | 7.0 | 33.0 | 15.0 | 25.0 | 4.0 | 40.0 |
| Content of E per 100 parts by weight of total of A + B + C |  |  | (parts by weight) | 0 | 0 | 0 | 0 | 0 | 0 | 0 | 0 | 0 |

TABLE 6

| | | | | Example 39 | Example 40 | Example 41 | Example 42 | Example 43 |
|---|---|---|---|---|---|---|---|---|
| Powder (X) | A | TTCP (D50: 1.1 μm) | (parts by weight) | | | | | 41.0 |
| | | TTCP (D50: 5.2 μm) | (parts by weight) | 10.0 | 70.0 | 75.0 | 5.0 | |
| | | TTCP (D50: 8.8 μm) | (parts by weight) | | | | | |
| | B | DCPA (D50: 0.3 μm) | (parts by weight) | | | | | |
| | | DCPA (D50: 1.1 μm) | (parts by weight) | 65.0 | 15.0 | 23.0 | 45.0 | 41.0 |
| | | DCPA (D50: 5.0 μm) | (parts by weight) | | | | | |
| | C | Calcium carbonate (D50: 0.5 μm) | (parts by weight) | | | | | |
| | | Calcium carbonate (D50: 2.6 μm) | (parts by weight) | 25.0 | 15.0 | 2.0 | 50.0 | 18.0 |
| | | Calcium carbonate (D50: 10.2 μm) | (parts by weight) | | | | | |
| | E | Na$_2$HPO$_4$ (D50: 5.2 μm) | (parts by weight) | | | | | |
| Total | | | (parts by weight) | 100.0 | 100.0 | 100.0 | 100.0 | 100.0 |
| Liquid (Y) | E | Na$_2$HPO$_4$ (D50: 5.2 μm) | (parts by weight) | | | | | |
| | D | Water | (parts by weight) | 100.0 | 100.0 | 100.0 | 100.0 | 100.0 |
| Total | | | (parts by weight) | 100.0 | 100.0 | 100.0 | 100.0 | 100.0 |
| Powder-to-liquid ratio (X/Y) | | | | 1.2 | 1.2 | 1.2 | 1.2 | 1.2 |
| Weight ratio ((A + B + C)/D) | | | | 1.2 | 1.2 | 1.2 | 1.2 | 1.2 |
| Dentinal tubule sealing ratio (initial) | | | (%) | 100 | 100 | 100 | 100 | 100 |
| Dentinal tubule sealing ratio (post-acid immersion) | | | (%) | 69.0 | 66.6 | 65.9 | 67.4 | 75.8 |
| Decrease ratio of dentinal tubule sealing ratio | | | (%) | 31.0 | 33.4 | 34.1 | 32.6 | 24.2 |
| Handling properties (II) | | | | A | A | A | A | A |
| Content of A per 100 parts by weight of total of A + B + C | | | (parts by weight) | 10.0 | 70.0 | 75.0 | 5.0 | 41.0 |
| Content of B per 100 parts by weight of total of A + B + C | | | (parts by weight) | 65.0 | 15.0 | 23.0 | 45.0 | 41.0 |
| Content of C per 100 parts by weight of total of A + B + C | | | (parts by weight) | 25.0 | 15.0 | 2.0 | 50.0 | 18.0 |
| Content of E per 100 parts by weight of total of A + B + C | | | (parts by weight) | 0 | 0 | 0 | 0 | 0 |

| | | | | Example 44 | Example 45 | Example 46 | Example 47 | Example 48 |
|---|---|---|---|---|---|---|---|---|
| Powder (X) | A | TTCP (D50: 1.1 μm) | (parts by weight) | | | | | |
| | | TTCP (D50: 5.2 μm) | (parts by weight) | | 41.0 | 41.0 | 41.0 | 41.0 |
| | | TTCP (D50: 8.8 μm) | (parts by weight) | 41.0 | | | | |
| | B | DCPA (D50: 0.3 μm) | (parts by weight) | | 41.0 | | | |
| | | DCPA (D50: 1.1 μm) | (parts by weight) | 41.0 | | | 41.0 | 41.0 |
| | | DCPA (D50: 5.0 μm) | (parts by weight) | | | 41.0 | | |
| | C | Calcium carbonate (D50: 0.5 μm) | (parts by weight) | | | | 18.0 | |
| | | Calcium carbonate (D50: 2.6 μm) | (parts by weight) | 18.0 | 18.0 | 18.0 | | |
| | | Calcium carbonate (D50: 10.2 μm) | (parts by weight) | | | | | 18.0 |
| | E | Na$_2$HPO$_4$ (D50: 5.2 μm) | (parts by weight) | | | | | |
| Total | | | (parts by weight) | 100.0 | 100.0 | 100.0 | 100.0 | 100.0 |

TABLE 6-continued

|  |  |  |  |  |  |  |  |  |
|---|---|---|---|---|---|---|---|---|
| Liquid (Y) | E | Na$_2$HPO$_4$ (D50: 5.2 μm) | (parts by weight) |  |  |  |  |  |
|  | D | Water | (parts by weight) | 100.0 | 100.0 | 100.0 | 100.0 | 100.0 |
| Total |  |  | (parts by weight) | 100.0 | 100.0 | 100.0 | 100.0 | 100.0 |
| Powder-to-liquid ratio (X/Y) |  |  |  | 1.2 | 1.2 | 1.2 | 1.2 | 1.2 |
| Weight ratio ((A + B + C)/D) |  |  |  | 1.2 | 1.2 | 1.2 | 1.2 | 1.2 |
| Dentinal tubule sealing ratio (initial) |  |  | (%) | 93.7 | 100 | 100 | 100 | 91.5 |
| Dentinal tubule sealing ratio (post-acid immersion) |  |  | (%) | 72.1 | 74.2 | 73.8 | 75.1 | 70.8 |
| Decrease ratio of dentinal tubule sealing ratio |  |  | (%) | 23.1 | 25.8 | 26.2 | 24.9 | 22.6 |
| Handling properties (II) |  |  |  | A | B | A | A | A |
| Content of A per 100 parts by weight of total of A + B + C |  |  | (parts by weight) | 41.0 | 41.0 | 41.0 | 41.0 | 41.0 |
| Content of B per 100 parts by weight of total of A + B + C |  |  | (parts by weight) | 41.0 | 41.0 | 41.0 | 41.0 | 41.0 |
| Content of C per 100 parts by weight of total of A + B + C |  |  | (parts by weight) | 18.0 | 18.0 | 18.0 | 18.0 | 18.0 |
| Content of E per 100 parts by weight of total of A + B + C |  |  | (parts by weight) | 0 | 0 | 0 | 0 | 0 |

TABLE 7

|  |  |  |  | Example 49 | Example 50 | Example 51 | Example 52 | Example 53 | Example 54 | Example 55 | Example 56 |
|---|---|---|---|---|---|---|---|---|---|---|---|
| Powder (X) | A | TTCP (D50: 1.1 μm) | (parts by weight) |  |  |  |  |  |  |  |  |
|  |  | TTCP (D50: 5.2 μm) | (parts by weight) | 41.0 | 41.0 | 38.3 | 40.7 | 36.0 | 41.0 | 41.0 | 41.0 |
|  |  | TTCP (D50: 8.8 μm) | (parts by weight) |  |  |  |  |  |  |  |  |
|  | B | DCPA (D50: 0.3 μm) | (parts by weight) |  |  |  |  |  |  |  |  |
|  |  | DCPA (D50: 1.1 μm) | (parts by weight) | 41.0 | 41.0 | 38.3 | 40.7 | 36.0 | 41.0 | 41.0 | 41.0 |
|  |  | DCPA (D50: 5.0 μm) | (parts by weight) |  |  |  |  |  |  |  |  |
|  | C | Calcium carbonate (D50: 0.5 μm) | (parts by weight) |  |  |  |  |  |  |  |  |
|  |  | Calcium carbonate (D50: 2.6 μm) | (parts by weight) | 18.0 | 18.0 | 16.2 | 17.9 | 15.0 | 18.0 | 18.0 | 18.0 |
|  |  | Calcium carbonate (D50: 10.2 μm) | (parts by weight) |  |  |  |  |  |  |  |  |
|  | E | Na$_2$HPO$_4$ (D50: 5.2 μm) | (parts by weight) |  |  | 7.2 | 0.7 | 13.0 |  |  |  |
| Total |  |  | (parts by weight) | 100.0 | 100.0 | 100.0 | 100.0 | 100.0 | 100.0 | 100.0 | 100.0 |
| Liquid (Y) | E | Na$_2$HPO$_4$ (D50: 5.2 μm) | (parts by weight) | 4.7 | 1.4 |  |  |  |  |  |  |
|  | D | Water | (parts by weight) | 95.3 | 98.6 | 100.0 | 100.0 | 100.0 | 100.0 | 100.0 | 100.0 |
| Total |  |  | (parts by weight) | 100.0 | 100.0 | 100.0 | 100.0 | 100.0 | 100.0 | 100.0 | 100.0 |
| Powder-to-liquid ratio (X/Y) |  |  |  | 1.2 | 1.2 | 1.2 | 1.2 | 1.2 | 0.5 | 0.7 | 1.7 |
| Weight ratio ((A + B + C)/D) |  |  |  | 1.26 | 1.22 | 1.11 | 1.19 | 1.04 | 0.5 | 0.7 | 1.7 |
| Dentinal tubule sealing ratio (initial) |  |  | (%) | 100 | 100 | 100 | 100 | 100 | 85.4 | 100 | 100 |
| Dentinal tubule sealing ratio (post-acid immersion) |  |  | (%) | 90.1 | 86.3 | 85.9 | 82.3 | 82.8 | 68.3 | 78.9 | 82.4 |
| Decrease ratio of dentinal tubule sealing ratio |  |  | (%) | 9.9 | 13.7 | 14.1 | 17.7 | 17.2 | 20.0 | 21.1 | 17.6 |
| Handling properties (II) |  |  |  | A | A | A | A | A | B | A | B |
| Content of A per 100 parts by weight of total of A + B + C |  |  | (parts by weight) | 41.0 | 41.0 | 41.3 | 41.0 | 41.4 | 41.0 | 41.0 | 41.0 |
| Content of B per 100 parts by weight of total of A + B + C |  |  | (parts by weight) | 41.0 | 41.0 | 41.3 | 41.0 | 41.4 | 41.0 | 41.0 | 41.0 |
| Content of C per 100 parts by weight of total of A + B + C |  |  | (parts by weight) | 18.0 | 18.0 | 17.5 | 18.0 | 17.2 | 18.0 | 18.0 | 18.0 |
| Content of E per 100 parts by weight of total of A + B + C |  |  | (parts by weight) | 3.9 | 1.2 | 7.8 | 0.7 | 14.9 | 0 | 0 | 0 |

TABLE 8

| | | | | Comp. Example 1 | Comp. Example 2 | Comp. Example 3 | Comp. Example 4 | Comp. Example 5 | Comp. Example 6 |
|---|---|---|---|---|---|---|---|---|---|
| Powder | A | TTCP (D50: 5.2 μm) | (parts by weight) | | | | | | |
| | | TTCP (D50: 8.8 μm) | (parts by weight) | 80.0 | 3.0 | 60.0 | 5.0 | 55.0 | 25.0 |
| | B | DCPA (D50: 1.1 μm) | (parts by weight) | 10.0 | 62.0 | 5.0 | 75.0 | 44.0 | 20.0 |
| | C | Calcium carbonate (D50: 2.6 μm) | (parts by weight) | 10.0 | 35.0 | 35.0 | 20.0 | 1.0 | 55.0 |
| | Phosphorus-free calcium compound other than C | Calcium hydroxide | (parts by weight) | | | | | | |
| | | Calcium oxide | (parts by weight) | | | | | | |
| | | Calcium silicate | (parts by weight) | | | | | | |
| | | Calcium nitrate | (parts by weight) | | | | | | |
| | | Calcium oxalate | (parts by weight) | | | | | | |
| | E | $Na_2HPO_4$ (D50: 5.2 μm) | (parts by weight) | | | | | | |
| Total | | | (parts by weight) | 100.0 | 100.0 | 100.0 | 100.0 | 100.0 | 100.0 |
| Liquid | E | $Na_2HPO_4$ (D50: 5.2 μm) | (parts by weight) | | | | | | |
| | D | Water | (parts by weight) | 100.0 | 100.0 | 100.0 | 100.0 | 100.0 | 100.0 |
| Total | | | (parts by weight) | 100.0 | 100.0 | 100.0 | 100.0 | 100.0 | 100.0 |
| Powder-to-liquid ratio (X/Y) | | | | 3.5 | 3.5 | 3.5 | 3.5 | 3.5 | 3.5 |
| Weight ratio ((A + B + C)/D) | | | | 3.5 | 3.5 | 3.5 | 3.5 | 3.5 | 3.5 |
| Handling properties (I) | | | | B | B | B | B | B | B |
| Initial compressive strength | | | (MPa) | 23.2 | 20.8 | Poor curing | 24.9 | 25.6 | Poor curing |
| Post-70° C./1-week treatment compressive strength | | | (MPa) | 11.4 | 10.7 | — | 13.1 | 14.2 | — |
| Decrease ratio of compressive strength | | | (%) | 50.9 | 48.6 | — | 47.4 | 44.5 | — |
| Content of A per 100 parts by weight of total of A + B + C | | | (parts by weight) | 80.0 | 3.0 | 60.0 | 5.0 | 55.0 | 25.0 |
| Content of B per 100 parts by weight of total of A + B + C | | | (parts by weight) | 10.0 | 62.0 | 5.0 | 75.0 | 44.0 | 20.0 |
| Content of C per 100 parts by weight of total of A + B + C | | | (parts by weight) | 10.0 | 35.0 | 35.0 | 20.0 | 1.0 | 55.0 |
| Content of E per 100 parts by weight of total of A + B + C | | | (parts by weight) | 0 | 0 | 0 | 0 | 0 | 0 |

| | | | | Comp. Example 7 | Comp. Example 8 | Comp. Example 9 | Comp. Example 10 | Comp. Example 11 |
|---|---|---|---|---|---|---|---|---|
| Powder | A | TTCP (D50: 5.2 μm) | (parts by weight) | | | | | |
| | | TTCP (D50: 8.8 μm) | (parts by weight) | 41.0 | 41.0 | 41.0 | 41.0 | 41.0 |
| | B | DCPA (D50: 1.1 μm) | (parts by weight) | 41.0 | 41.0 | 41.0 | 41.0 | 41.0 |
| | C | Calcium carbonate (D50: 2.6 μm) | (parts by weight) | | | | | |
| | Phosphorus-free calcium compound other than C | Calcium hydroxide | (parts by weight) | 18.0 | | | | |
| | | Calcium oxide | (parts by weight) | | 18.0 | | | |
| | | Calcium silicate | (parts by weight) | | | 18.0 | | |
| | | Calcium nitrate | (parts by weight) | | | | 18.0 | |
| | | Calcium oxalate | (parts by weight) | | | | | 18.0 |
| | E | $Na_2HPO_4$ (D50: 5.2 μm) | (parts by weight) | | | | | |
| Total | | | (parts by weight) | 100.0 | 100.0 | 100.0 | 100.0 | 100.0 |

TABLE 8-continued

|  |  |  |  |  |  |  |  |  |
|---|---|---|---|---|---|---|---|---|
| Liquid | E | Na$_2$HPO$_4$ (D50: 5.2 μm) | (parts by weight) | 12.0 | 12.0 | 12.0 | 12.0 | 12.0 |
|  | D | Water | (parts by weight) | 88.0 | 88.0 | 88.0 | 88.0 | 88.0 |
| Total |  |  | (parts by weight) | 100.0 | 100.0 | 100.0 | 100.0 | 100.0 |
| Powder-to-liquid ratio (X/Y) |  |  |  | 3.5 | 3.5 | 3.5 | 3.5 | 3.5 |
| Weight ratio ((A + B + C)/D) |  |  |  | — | — | — | — | — |
| Handling properties (I) |  |  |  | — | — | — | — | — |
| Initial compressive strength |  |  | (MPa) | Poor curing | Poor curing | Poor curing | Poor curing | Poor curing |
| Post-70° C./1-week treatment compressive strength |  |  | (MPa) | — | — | — | — | — |
| Decrease ratio of compressive strength |  |  | (%) | — | — | — | — | — |
| Content of A per 100 parts by weight of total of A + B + C |  |  | (parts by weight) | 50.0 | 50.0 | 50.0 | 50.0 | 50.0 |
| Content of B per 100 parts by weight of total of A + B + C |  |  | (parts by weight) | 50.0 | 50.0 | 50.0 | 50.0 | 50.0 |
| Content of C per 100 parts by weight of total of A + B + C |  |  | (parts by weight) | 0 | 0 | 0 | 0 | 0 |
| Content of E per 100 parts by weight of total of A + B + C |  |  | (parts by weight) | 4.2 | 4.2 | 4.2 | 4.2 | 4.2 |

TABLE 9

|  |  |  |  | Comp. Example 12 | Comp. Example 13 | Comp. Example 14 | Comp. Example 15 | Comp. Example 16 |
|---|---|---|---|---|---|---|---|---|
| Powder | A | TTCP (D50: 5.2 μm) | (parts by weight) | 80.0 | 3.0 | 60.0 | 5.0 | 55.0 |
|  |  | TTCP (D50: 8.8 μm) | (parts by weight) |  |  |  |  |  |
|  | B | DCPA (D50: 1.1 μm) | (parts by weight) | 10.0 | 62.0 | 5.0 | 75.0 | 44.0 |
|  | C | Calcium carbonate (D50: 2.6 μm) | (parts by weight) | 10.0 | 35.0 | 35.0 | 20.0 | 1.0 |
|  | Phosphorus-free calcium compound other than C | Calcium hydroxide | (parts by weight) |  |  |  |  |  |
|  |  | Calcium oxide | (parts by weight) |  |  |  |  |  |
|  |  | Calcium silicate | (parts by weight) |  |  |  |  |  |
|  |  | Calcium nitrate | (parts by weight) |  |  |  |  |  |
|  |  | Calcium oxalate | (parts by weight) |  |  |  |  |  |
|  | E | Na$_2$HPO$_4$ (D50: 5.2 μm) | (parts by weight) |  |  |  |  |  |
| Total |  |  | (parts by weight) | 100.0 | 100.0 | 100.0 | 100.0 | 100.0 |
| Liquid | E | Na$_2$HPO$_4$ (D50: 5.2 μm) | (parts by weight) |  |  |  |  |  |
|  | D | Water | (parts by weight) | 100.0 | 100.0 | 100.0 | 100.0 | 100.0 |
| Total |  |  | (parts by weight) | 100.0 | 100.0 | 100.0 | 100.0 | 100.0 |
| Powder-to-liquid ratio (X/Y) |  |  |  | 1.2 | 1.2 | 1.2 | 1.2 | 1.2 |
| Weight ratio ((A + B + C)/D) |  |  |  | 1.2 | 1.2 | 1.2 | 1.2 | 1.2 |
| Dentinal tubule sealing ratio (initial) |  |  | (%) | 100 | 100 | 68.5 | 100 | 100 |
| Dentinal tubule sealing ratio (post-acid immersion) |  |  | (%) | 50.1 | 54.5 | 20.5 | 48.3 | 57.3 |
| Decrease ratio of dentinal tubule sealing ratio |  |  | (%) | 49.9 | 45.5 | 70.1 | 51.7 | 42.7 |
| Handling properties (II) |  |  |  | A | A | A | A | A |
| Content of A per 100 parts by weight of total of A + B + C |  |  | (parts by weight) | 80.0 | 3.0 | 60.0 | 5.0 | 55.0 |
| Content of B per 100 parts by weight of total of A + B + C |  |  | (parts by weight) | 10.0 | 62.0 | 5.0 | 75.0 | 44.0 |
| Content of C per 100 parts by weight of total of A + B + C |  |  | (parts by weight) | 10.0 | 35.0 | 35.0 | 20.0 | 1.0 |
| Content of E per 100 parts by weight of total of A + B + C |  |  | (parts by weight) | 0 | 0 | 0 | 0 | 0 |

TABLE 9-continued

|  |  |  |  | Comp. Example 17 | Comp. Example 18 | Comp. Example 19 | Comp. Example 20 | Comp. Example 21 |
|---|---|---|---|---|---|---|---|---|
| Powder | A | TTCP (D50: 5.2 μm) | (parts by weight) | 25.0 | 41.0 | 41.0 | 41.0 | 41.0 |
|  |  | TTCP (D50: 8.8 μm) | (parts by weight) |  |  |  |  |  |
|  | B | DCPA (D50: 1.1 μm) | (parts by weight) | 20.0 | 41.0 | 41.0 | 41.0 | 41.0 |
|  | C | Calcium carbonate (D50: 2.6 μm) | (parts by weight) | 55.0 |  |  |  |  |
|  | Phosphorus-free calcium compound other than C | Calcium hydroxide | (parts by weight) |  | 18.0 |  |  |  |
|  |  | Calcium oxide | (parts by weight) |  |  | 18.0 |  |  |
|  |  | Calcium silicate | (parts by weight) |  |  |  | 18.0 |  |
|  |  | Calcium nitrate | (parts by weight) |  |  |  |  | 18.0 |
|  |  | Calcium oxalate | (parts by weight) |  |  |  |  |  |
|  | E | $Na_2HPO_4$ (D50: 5.2 μm) | (parts by weight) |  |  |  |  |  |
| Total |  |  | (parts by weight) | 100.0 | 100.0 | 100.0 | 100.0 | 100.0 |
| Liquid | E | $Na_2HPO_4$ (D50: 5.2 μm) | (parts by weight) |  |  |  |  |  |
|  | D | Water | (parts by weight) | 100.0 | 100.0 | 100.0 | 100.0 | 100.0 |
| Total |  |  | (parts by weight) | 100.0 | 100.0 | 100.0 | 100.0 | 100.0 |
| Powder-to-liquid ratio (X/Y) |  |  |  | 1.2 | 1.2 | 1.2 | 1.2 | 1.2 |
| Weight ratio ((A + B + C)/D) |  |  |  | 1.2 | — | — | — | — |
| Dentinal tubule sealing ratio (initial) |  |  | (%) | 63.9 | 58.2 | 66.9 | 53.1 | 49.2 |
| Dentinal tubule sealing ratio (post-acid immersion) |  |  | (%) | 25.2 | — | — | — | — |
| Decrease ratio of dentinal tubule sealing ratio |  |  | (%) | 60.6 | — | — | — | — |
| Handling properties (II) |  |  |  | A | — | — | — | — |
| Content of A per 100 parts by weight of total of A + B + C |  |  | (parts by weight) | 25.0 | 50.0 | 50.0 | 50.0 | 50.0 |
| Content of B per 100 parts by weight of total of A + B + C |  |  | (parts by weight) | 20.0 | 50.0 | 50.0 | 50.0 | 50.0 |
| Content of C per 100 parts by weight of total of A + B + C |  |  | (parts by weight) | 55.0 | 0 | 0 | 0 | 0 |
| Content of E per 100 parts by weight of total of A + B + C |  |  | (parts by weight) | 0 | 0 | 0 | 0 | 0 |

TABLE 10

|  |  |  |  | Comp. Example 22 | Comp. Example 23 | Comp. Example 24 | Comp. Example 25 | Comp. Example 26 |
|---|---|---|---|---|---|---|---|---|
| Powder | A | TTCP (D50: 5.2 μm) | (parts by weight) |  |  |  |  | 66.0 |
|  |  | TTCP (D50: 8.8 μm) | (parts by weight) | 65.0 | 72.9 |  |  |  |
|  | B | DCPA (D50: 1.1 μm) | (parts by weight) | 35.0 | 27.1 | 67.0 | 84.0 | 25.0 |
|  | C | Calcium carbonate (D50: 2.6 μm) | (parts by weight) |  |  | 33.0 |  |  |
|  | Phosphorus-free calcium compound other than C | Calcium hydroxide | (parts by weight) |  |  |  | 0.8 |  |
|  |  | Calcium oxide | (parts by weight) |  |  |  |  |  |
|  |  | Calcium silicate | (parts by weight) |  |  |  |  |  |

TABLE 10-continued

|  |  |  |  | Comp. Example 22 | Comp. Example 23 | Comp. Example 24 | Comp. Example 25 | Comp. Example 26 |
|---|---|---|---|---|---|---|---|---|
|  |  | Calcium nitrate | (parts by weight) |  |  |  |  |  |
|  |  | Calcium oxalate | (parts by weight) |  |  |  |  |  |
|  | E | $Na_2HPO_4$ (D50: 5.2 μm) | (parts by weight) |  |  |  | 15.2 | 9.0 |
| Total |  |  | (parts by weight) | 100.0 | 100.0 | 100.0 | 100.0 | 100.0 |
| Liquid | E | $Na_2HPO_4$ (D50: 5.2 μm) | (parts by weight) |  | 2.8 | 14.2 |  |  |
|  | D | Water | (parts by weight) | 100.0 | 97.2 | 85.8 | 100.0 | 100.0 |
| Total |  |  | (parts by weight) | 100.0 | 100.0 | 100.0 | 100.0 | 100.0 |
| Powder-to-liquid ratio (X/Y) |  |  |  | 4.0 | 3.5 | 3.5 | 1.9 | 1.3 |
| Weight ratio ((A + B + C)/D) |  |  |  | — | — | — | — | — |
| Handling properties (I) |  |  |  | C | B | B | — | — |
| Initial compressive strength |  |  | (MPa) | 41.6 | 51.2 | 42.4 | — | — |
| Post-70° C./1-week treatment compressive strength |  |  | (MPa) | 20.5 | 22.7 | 18.6 | — | — |
| Decrease ratio of compressive strength |  |  | (%) | 50.7 | 55.7 | 56.1 | — | — |
| Dentinal tubule sealing ratio (initial) |  |  | (%) | — | — | — | 100 | 100 |
| Dentinal tubule sealing ratio (post-acid immersion) |  |  | (%) | — | — | — | 53.1 | 65.2 |
| Decrease ratio of dentinal tubule sealing ratio |  |  | (%) | — | — | — | 46.9 | 34.8 |
| Handling properties (II) |  |  |  | — | — | — | A | A |
| Content of A per 100 parts by weight of total of A + B + C |  |  | (parts by weight) | 65.0 | 72.9 | 0 | 0 | 72.5 |
| Content of B per 100 parts by weight of total of A + B + C |  |  | (parts by weight) | 35.0 | 27.1 | 67.0 | 100.0 | 27.5 |
| Content of C per 100 parts by weight of total of A + B + C |  |  | (parts by weight) | 0 | 0 | 33.0 | 0 | 0 |
| Content of E per 100 parts by weight of total of A + B + C |  |  | (parts by weight) | 0 | 0.8 | 4.1 | 18.1 | 9.9 |

INDUSTRIAL APPLICABILITY

The curable calcium phosphate composition of the present invention for biological hard tissue repair is suitable for use in: bone repair materials such as a bone filling material and a bone cement; and dental materials such as a filling restorative material, a lining material, a luting material, a temporary sealing material, a root canal filling material, a temporary cementation material, a coating material, a sealant, and a dentinal tubule sealing material.

The invention claimed is:

1. A curable calcium phosphate composition for biological hard tissue repair, comprising tetracalcium phosphate particles (A), calcium hydrogen phosphate particles (B), calcium carbonate particles (C), and water (D),
   wherein the curable calcium phosphate composition comprises from 5 to 75 parts by weight of the tetracalcium phosphate particles (A), from 10 to 70 parts by weight of the calcium hydrogen phosphate particles (B), and from 2 to 50 parts by weight of the calcium carbonate particles (C) per 100 parts by weight of the total of the tetracalcium phosphate particles (A), the calcium hydrogen phosphate particles (B), and the calcium carbonate particles (CX
   wherein the tetracalcium phosphate particles (A) have an average particle diameter of from 0.5 to 30 um the calcium hydrogen phosphate particles (B) have an average particle diameter of from 0.1 to 75 um, and the calcium carbonate particles (C) have an average particle diameter of from 0.1 to 30 um,
   and wherein a weight ratio, (A+B+C)/D, of the total of the tetracalcium phosphate particles (A), the calcium hydrogen phosphate particles (B), and the calcium carbonate particles (C) to the water (D) is from 1.8 to 5.0.

2. The curable calcium phosphate composition according to claim 1, further comprising from 0.5 to 15 parts by weight of an alkali metal phosphate (E) per 100 parts by weight of the total of the tetracalcium phosphate particles (A), the calcium hydrogen phosphate particles (B), and the calcium carbonate particles (C).

3. The curable calcium phosphate composition according to claim 2, wherein the alkali metal phosphate (E) is at least one selected from the group consisting of disodium hydrogen phosphate and sodium dihydrogen phosphate.

4. A bone repair material comprising the curable calcium phosphate composition according to claim 1.

5. A dental filling restorative material comprising the curable calcium phosphate composition according to claim 1.

6. A dental lining material comprising the curable calcium phosphate composition according to claim 1.

7. A dental luting material comprising the curable calcium phosphate composition according to claim 1.

8. A dental temporary sealing material comprising the curable calcium phosphate composition according to claim 1.

9. A dental sealant comprising the curable calcium phosphate composition according to claim 1.

10. A dental temporary cementation material comprising the curable calcium phosphate composition according to claim 1.

11. A dental root canal filling material comprising the curable calcium phosphate composition according to claim 1.

12. A dental coating material comprising the curable calcium phosphate composition according to claim 1.

13. The curable calcium phosphate composition according to claim 1, wherein a weight ratio, (A+B+C)/D, of the total of the tetracalcium phosphate particles (A), the calcium hydrogen phosphate particles (B), and the calcium carbonate particles (C) to the water (D) is from 0.5 to 1.8.

14. A dental dentinal tubule sealing material comprising the curable calcium phosphate composition according to claim 13.

* * * * *